United States Patent
Zhang et al.

(10) Patent No.: US 6,266,560 B1
(45) Date of Patent: Jul. 24, 2001

(54) ELECTRICALLY ASSISTED TRANSDERMAL METHOD AND APPARATUS FOR THE TREATMENT OF ERECTILE DYSFUNCTION

(75) Inventors: Lei Zhang; Gunter A. Hofmann, both of San Diego; Dietmar Rabussay, Solana Beach, all of CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

(21) Appl. No.: 09/336,400

(22) Filed: Jun. 18, 1999

Related U.S. Application Data
(60) Provisional application No. 60/089,869, filed on Jun. 19, 1998.

(51) Int. Cl.[7] .................................................. A61N 1/44
(52) U.S. Cl. ........................................................ 604/20
(58) Field of Search ................................ 607/39, 43, 20

(56) References Cited

U.S. PATENT DOCUMENTS

| | | |
|---|---|---|
| 4,742,833 | 5/1988 | Barsom . |
| 5,270,323 * | 12/1993 | Milne, Jr. et al. ........... 604/20 |
| 5,464,386 * | 11/1995 | Hofmann ...................... 604/20 |
| 5,571,118 * | 11/1996 | Boutos ......................... 607/143 |
| 5,622,944 * | 4/1997 | Hale et al. .................... 604/20 |

FOREIGN PATENT DOCUMENTS

0049515 * 8/1911 (AT) ........................... 607/143

* cited by examiner

Primary Examiner—William E. Kamm
(74) Attorney, Agent, or Firm—Gray Cary Ware & Freidenrich LLP; Lisa A. Haile

(57) ABSTRACT

A non-invasive method is provided for treating erectile dysfunction using electroporation enhanced with delivery of a vasoactive or androgenic composition applied to the penis which affords an alternative treatment for patients afflicted with erectile dysfunction (ED). Sufficient electric pulses temporarily create new pathways in the penile skin thereby driving a composition, such as a vasoactive or androgenic medication, into the corporal cavernosum.

23 Claims, 18 Drawing Sheets

| SET VOLTAGE | 0 NO PAIN | 1 TO 2 MILD | 3 TO 4 DISCOMFORTING | 5 (BETWEEN) | 6 TO 7 DISTRESSING | 8 TO 9 HORRIBLE | 10 EXCRUCIATING | TOTAL N |
|---|---|---|---|---|---|---|---|---|
| 50 V | 3 | 10 | 6 | 1 | 0 | 0 | 0 | 20 |
| 60 V | 1 | 8 | 10 | 0 | 1 | 0 | 0 | 20 |
| 70 V | 1 | 2 | 10 | 5 | 1 | 1 | 0 | 20 |
| 80 V | 0 | 1 | 10 | 4 | 2 | 3 | 0 | 20 |
| TOTAL N | 5 | 21 | 36 | 10 | 4 | 4 | 0 | 80 |

FIG. 13

ELECTRICALLY ASSISTED TRANSDERMAL METHOD AND APPARATUS FOR THE TREATMENT OF ERECTILE DYSFUNCTION

This application claims benefit of provisional application Ser. No. 60/089,869 filed Jun. 19, 1998.

FIELD OF THE INVENTION

The present invention relates generally to erectile function, and more specifically to methods and an apparatus for treatment of erectile dysfunction.

BACKGROUND OF THE INVENTION

Penile erection depends on the relaxation of cavernosal smooth muscle. Relaxation of the trabecular smooth muscle permits dilation of the lacunar spaces, causing engorgement of the penis. Inflow of blood at the systemic blood pressure to the lacunar spaces expands the relaxed trabeculae against the tunica albuginea. This compresses the subtunical venules, reduces venous outflow from the lacunar space, and elevates lacunar space pressure, making the penis rigid. Contraction of the cavernosal smooth muscle leads to penile detumescence. This results in a reduction of arterial inflow and a collapse of the lacunar spaces with decompression of subtunical venules and increased venous outflow from the lacunar spaces, returning the penis to the flaccid state.

Penile erectile dysfunction is a common medical disorder. It has been estimated that it is prevalent in 2% of men aged 40 years, which an increase to over 50% in men over the age of 70 years, affecting some 10 to 20 million men in the US alone. Intracavernosal injection of vasodilators, such as prostaglandin E1 (PGE1, alprostadil; CAVERJECT™/ Upjohn-for intracavernosal use), is a commonly used treatment for erectile dysfunction (Porst, J. Urol. 155(1996) 802–812). When injected into the penis, prostaglandin E1 can induce an erection within a few minutes in up to 80% of cases, and acts by relaxing the smooth muscle of the penis. Different formulations of prostaglandin E1 are now available and have been compared (Vanderschueren et al., J. Urol. 154(1995) 1744–1747). Mechanism and side effects have been studied (Granata et al., Psychosom. Med. 57 (1995) 336–344; Italiano et al., Pharmacol. Res. 31 (1995) 313–317). Although effective, the drawbacks of intracavernosal injection therapy include the inconvenience of injection, discomfort, stress and pain during injection and penile scarring (Gana et al., Curr. Ther. Res. 57 (1996) 700–710; Chen et al., J. Urol. 155 (1996) 138–140). As prostaglandins undergo first pass metabolism and adverse reactions such as diarrhea follow oral use, they cannot be administered orally.

Other methods for treating erectile dysfunction include malleable (bendable) or inflatable penile implants or prostheses, which are manufactured by several different companies. However, such devices require surgery. The use of penile suppositories, in which a drug is delivered transurethrally, (alprostadil in MUSE; medicated urethral system for erections), can be painful or less effective. Oral corporal pharmacotherapy also has been used. Apomorphine treatment, in which a pellet is placed under the tongue for absorption into the blood stream, works by stimulating receptors in the brain which may then result in an erection five to twenty minutes after administration. Sildenafil citrate (VIAGRA™, Pfizer) has become available more recently and has been shown to help about 70% of men with impotency problems. However, in patients with preexisting cardiovascular disease, there is a potential for cardiac risk of sexual activity associated with VIAGRA use. Further, patients taking any medicines that contain nitrates, which are often used as treatments for angina (chest pain due to heart disease), cannot take VIAGRA. Moreover, not all patients respond to VIAGRA treatment.

Topical/transdermal delivery of vasodilators that stimulate erectile function is another possibility for treating erectile dysfunction (e.g., hydralazine; U.S. Pat. No. 4,801,587). Transdermal delivery of prostaglandins has been shown to be feasible (Watkinson et al., Int. J. Pharm. 74 (1991) 229–236., Uekama et al., J. Pharm. Pharmacol. 44 (1992) 119–121), and delivery is facilitated by penetration enhancers. It has been shown that PGE1 permeated across hairless mouse skin in-vitro when delivered by iontophoresis, but not by passive transport (aqueous solution used; Saeki et al., Int. J. Pharm. Therapeutics 36 (1996) 525–529). However, the lag time of absorption may be too long for treatment of erectile disorders, as a response within 5–20 minutes is desired. When 500 microgram of PGE1 was applied to the genital area, immediate erection could not be obtained (Chiang et al., Ann. Acad. Med. Singapore 24 (1995) 767–769).

Thus, in view of the problems associated with current methods for treating erectile dysfunction by injectable and systemic pharmacotherapies and prostheses, a need exists for the development of alternative methods for treating erectile dysfunction. The present invention satisfies this need and provides related advantages as well.

SUMMARY OF THE INVENTION

The present invention is based on the development of a non-invasive method and apparatus for delivery of drugs or genes into the penile erectile tissue to induce or enhance penile erection, which affords an alternative treatment for patients afflicted with erectile dysfunction (ED). Sufficient electric pulses temporarily create new pathways in the penile skin thereby driving a composition, such as a vasoactive or androgenic medication, into the corporal cavernosum.

In a first embodiment, the invention provides an electrical apparatus for treating erectile dysfunction or inducing or enhancing erectile function non-invasively in a subject. The apparatus includes a cuff capable of conforming to the shape of a penis; and a pulse applicator connected to said cuff capable of applying an electric pulse of sufficient strength and duration to the penis for transdermally introducing a composition into the penis.

In another embodiment, the invention includes a method for treating erectile dysfunction or for inducing, enhancing or maintaining erectile function in a subject, comprising applying an electric pulse to the penis substantially contemporaneously with a vasoactive or androgenic composition, said electric pulse having sufficient strength and duration for transdermally introducing an effective amount of the composition into the penis, thereby treating erectile dysfunction or inducing, promoting or enhancing erectile function.

In yet another embodiment, the invention includes a method for preventing or inhibiting impotence in a subject including applying an electric pulse to the penis substantially contemporaneously with a vasoactive or androgenic composition, said electric pulse having sufficient strength and duration for transdermally introducing an effective amount of the composition into the penis for preventing or inhibiting impotence.

The invention further includes a method for delivering a composition into the penis of a subject including applying an electric pulse to the penis substantially contemporaneously with the composition, said electric pulse having sufficient strength and duration for transdermally introducing the composition into the penis in an amount greater than passive diffusion.

The invention also includes a kit for treating erectile dysfunction or inducing or enhancing erectile function. The kit includes, for example, a package having an electrical apparatus for treating erectile dysfunction or inducing or enhancing erectile function of a subject; and instructions for use.

BRIEF DESCRIPTION OF THE DRAWINGS

FIG. 13 shows that electropulsing at a strength and duration to introduce a composition into the rabbit penis is well tolerated by human subjects.

DETAILED DESCRIPTION OF THE INVENTION

Figure 1:
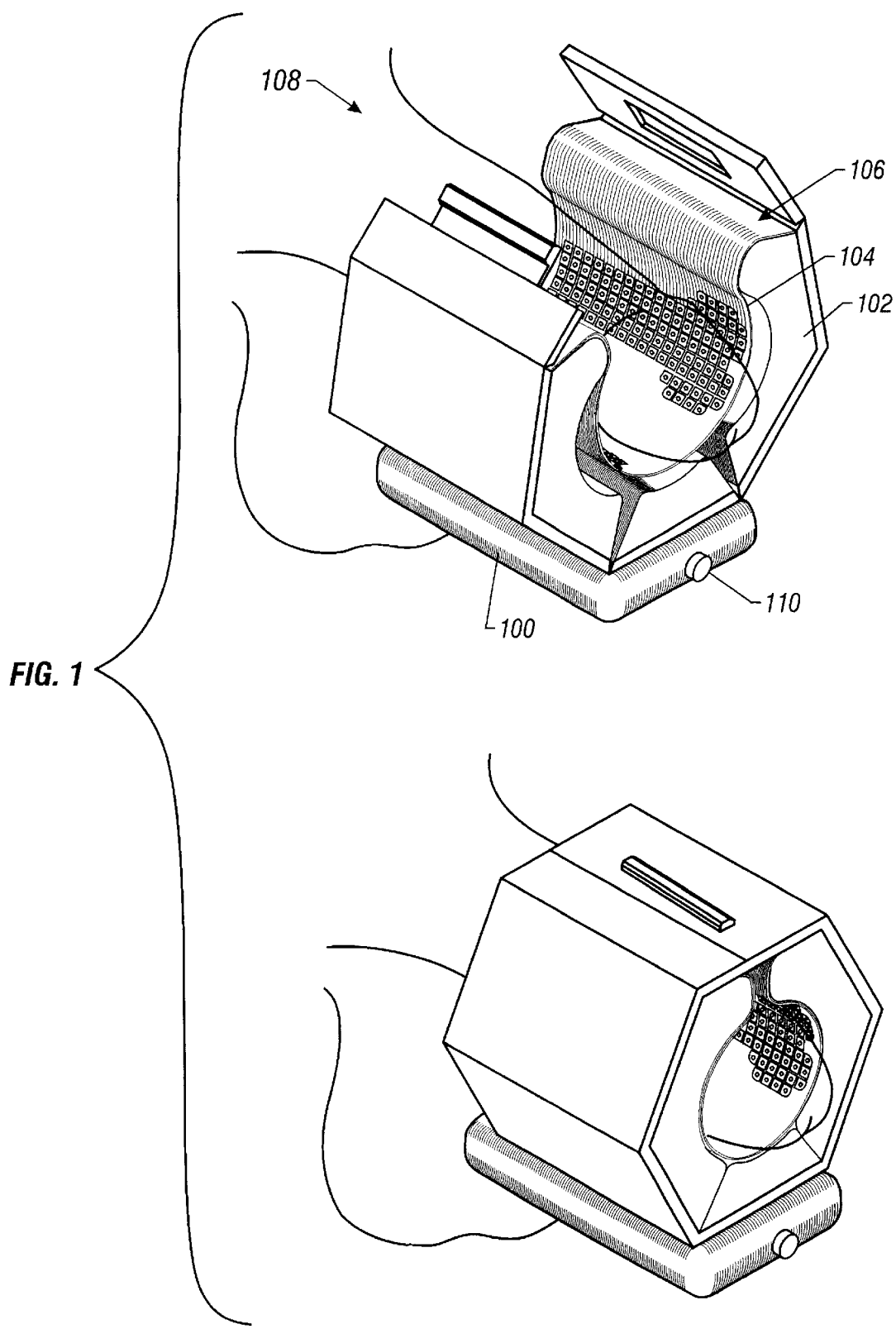
FIG. 1 shows an exemplary electrical apparatus for transdermally introducing compositions into the penis comprising a cuff, a pulse applicator and a pulse generator.

The present invention is based upon the seminal discovery that applying a composition to the penile shaft or glans in conjunction with applying an electrical impulse to the penis is effective for introducing compositions into the penis. The invention therefore provides an electrical apparatus for transdermally introducing compositions into the penis and methods for introducing compositions into the penis. A method of the invention includes applying an electric pulse of a sufficient strength and duration to the penile shaft or glans substantially contemporaneously with a vasodilator or androgenic composition, thereby transdermally introducing the composition into the penis. A method of the invention in which an effective amount of such a composition is transdermally introduced into the penis is useful for treating erectile dysfunction or for inducing, enhancing or maintaining erectile function.

The electrical apparatus and the methods of the invention are advantageous in several respects. The apparatus and the methods allow for rapid and non-invasive delivery of a drug into the penis without the pain and penile fibrosis/scarring that results from needle injection. The dose of medication needed for local treatment as compared to systemic treatment is generally lower thereby minimizing or prevent side effects or other problems associated with systemic drug delivery. Thus, the apparatus and the methods of the invention are particularly applicable for treating erectile dysfunction or for inducing, enhancing or maintaining erectile function in subjects having a low pain tolerance, who easily scar or in which the use of systemic drugs is not possible or is otherwise undesirable. The invention apparatus and methods are additionally advantageous when used in combination with other techniques or apparatus (e.g., iontophoresis (IPH), vibration, phonophoresis, pharmacotherapeutics (optionally, liposome encapsulated), penile venous flow restriction devices,) as the combination can produce an additive or synergistic effect so that maximal therapeutical effects for treating erectile dysfunction or for inducing or enhancing erectile function are produced. For example, successive electropulsing of one vasodilating composition into the penis followed by a different composition, or a mixture of different vasodilating compositions can produce a greater effect than electropulsing a single vasodilating composition alone. Electropulsing the penis with a vasoactive composition, followed by iontophoresis, can produce a greater therapeutic effect than either applying the pulse or iontophoresis alone. Similarly, electropulsing combined with administering a drug for treating erectile dysfunction (e.g., VIAGRA™), at doses lower than those normally associated with clinical efficacy, can produce an additive or synergistic effect greater than that produced by penile transdermal drug introduction or VIAGRA™ administration alone, while minimizing side effects due to the lower dose. Furthermore, electroincorporation (see, e.g., U.S. Pat. No. 5,464,386, which is hereby incorporated herein in its entirety by reference), or electropulsing in combination with IPH and liposomal formulation can enhance delevirey significantly. (see, e.g., Badkar, et al., Drug Delivery 6 (1000) 111–115).

As used herein, the terms "impulse," "pulse," "electrical impulse," "electrical pulse," "electric pulse," "electropulse" and grammatical variations thereof are interchangeable and all refer to an electrical stimulus. Although the various terms are frequently used herein in the singular, the singular forms of the terms include multiple pulses. Preferred electrical impulses are pulsed electric fields applied via electroporation. The pulse can be unipolar, bipolar, exponential or square wave form.

The term "erectile dysfunction" is used broadly herein, and refers to either an acute or chronic inability to achieve or maintain an erection of sufficient rigidity for sexual intercourse. Thus, the term includes severe cases of chronic impotence as well as single episodes of impotence in a subject not generally characterized as impotent. The term "treating" when use in reference to erectile dysfunction further includes "preventing" or "inhibiting" erectile dysfunction.

As used herein, the term "erectile function" refers to either an induction of penile tumescence sufficient to achieve sexual intercourse, to an increased or enhanced penile tumescence in a penis that already exhibits tumescence, or to maintenance of penile tumescence. Generally, erectile function "induced, enhanced or maintained" will be that sufficient for sexual intercourse.

As used herein, the term "transdermally introducing" and grammatical variations thereof, refers to the delivery of a composition into the skin, through/across the skin, or a combination thereof. An electric pulse that transdermally introduces a composition into the penis is believed to overcome the resistance of the skin barrier or alter the permeability of tunica albuginia. Thus, in a method of the invention in which an androgenic or vasoactive composition is "transdermally introduced" into the penis, the composition is driven into or through/across the penile skin. The "transdermally introduced" composition is likely driven into the corporal cavernosum, or into the blood supplying the corporal cavernosum by the pulse(s), to affect the erectile tissue.

As used herein, the term "subject" refers to any animal that has a blood vessel. It is envisioned that the methods for inducing or increasing vasodilation of a vessel and the methods for inducing or increasing the flow of fluid through a vessel described herein can be performed on any animal. Preferably, the subject is a human.

The invention provides an electrical apparatus for treating erectile function or for inducing, enhancing or maintaining erectile function. The apparatus comprises a cuff capable of conforming to the shape of a penis and a pulse applicator connected to said cuff capable of applying an electric pulse of sufficient strength and duration to the penis for transdermally introducing a composition into the penis.

An exemplary hand-held electrical apparatus, comprising a mini pulse generator 100 physically connected to a cuff 102 in association with an electrode containing pulse applicator (or sheath) 104, is shown in FIG. 1. The cuff shape will preferably be cylindrical, although other shapes can be used so long as the shape is ergonomically compatible with the penis and can function as described herein. The exemplary pulse applicator comprises a sheath, optionally disposable, that conforms to the cuff shape (illustrated but not limited to FIGS. 1 and 2); the sheath contains an electrode 106 on the inner surface. Depending on the formulation of the composition to be transdermally introduced, the electrode can be an insulated or porous meander electrode; a meander electrode is an interweaving array of metal fingers coated on a thin film, such as plastic, which can be placed on skin. The sheath is connected to the mini generator via contacts on the outer surface of the sheath. The sheath enables one or both sides of the penile midshaft, penile glans or both midshaft and glans to be in contact with the electrode, while generally avoiding urethra contact with the electrode. Prior to use, the sheath is positioned in the cuff so that contacts located on the outer surface are made with the mini generator, and the inner surface of the sheath is positioned to be in contact with the penis; a desired composition is administered, preferably topically, to the penis. In operation, the penis is placed longitudinally in the cuff in contact with the electrodes (as disposed within the sheath) and the cuff is closed about the penis; the exemplary electrical apparatus has an integral snap-closure mechanism 108 to secure the cuff in the closed position thereby ensuring good contact between the electrodes and the penile glans, shaft, or both, as is shown in FIG. 1. One or more appropriate electric pulses are then applied, preferably a pulsed electric field, by depressing an activator button 110; the exemplary electrical apparatus has the activator button positioned on the mini-generator.

Figure 3:
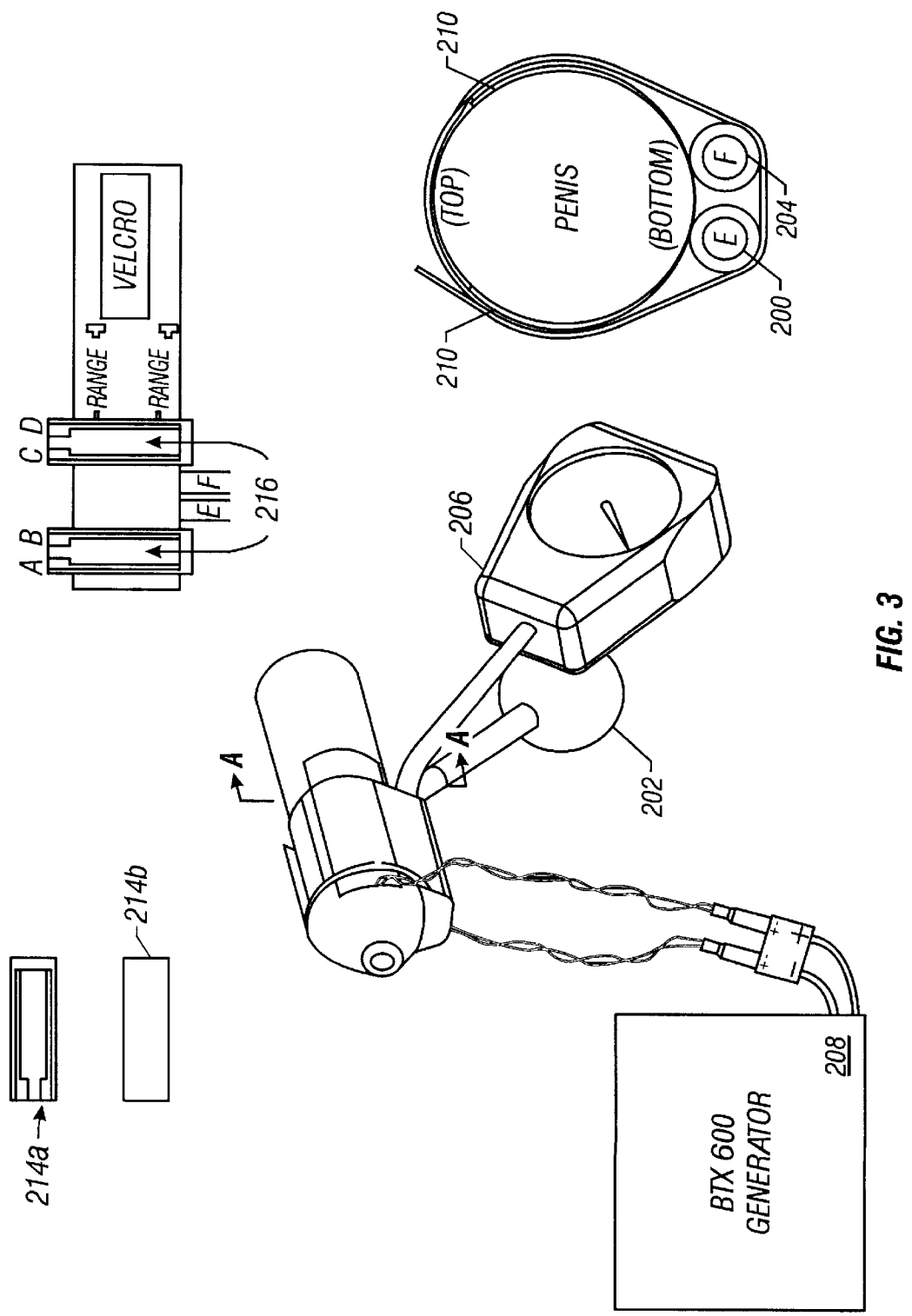
FIG. 3 shows another exemplary electrical apparatus for transdermally introducing compositions into the penis for feasibility study on patients (cuff type with integral pulse applicator).

The aforementioned invention apparatus shown in FIG. 1 is not meant to be limiting. Thus, other apparatus, additional functional components and variations thereof are specifically contemplated herein. For example, a second exemplary apparatus is shown in FIG. 3 that includes several additional components such as a pressure applicator tube 200 (to improve contact between penile skin and electrode, or to exert pressure on the penis thereby increasing transdermal introduction of a composition into the penis), a means for applying pressure (e.g., a bulb 202), a pressure sensor tube 204 and a sensor gauge 206 (e.g,. indicating if there is a good contact between penile skin and electrode). In the depicted embodiment, an infant blood pressure cuff was employed, as it contains a pressure tube and sensor. The remaining components of the invention assembly are essentially the same as those described and depicted in FIG. 1. For example, there is a sheath (or pulse applicator) 210, comprising electrodes 216, disposed within a meander strip 214, having an elctrode side 214a and a back side 214b. As shown in FIG. 3, the pulse generator 208, although operatively connected to the pulse applicator is not physically attached to the sheath 210 or to the cuff, as in the mini-apparatus exemplified in FIG. 1. Thus, an invention electrical apparatus may or may not be physically attached to the pulse generator, but only need be operatively connected.

Additional functional components that can be added to the invention electrical apparatus include, for example, an iontophoresis unit (IPH), which can be used in combination with an electrical impulse to transdermally introduce a greater amount of the composition into the penis than pulsing alone, or that can drive the composition deeper into the penis, if desired. A switching unit, such as an automated switch, optionally programmable, could be used to control the time between applying the impulse and applying IPH, as well as optionally controlling the time during which IPH is applied. Each parameter will be determined by the composition introduced, the desired effect, the concentration etc. In one aspect of this embodiment, electrodes on either side of the penis can be operated by an electroporation unit and an IPH unit respectively in a sequential manner. More specifically, two electrodes can be disposed on either side of the penis (e.g., electrodes 1 and 2 on the left side and electrodes 3 and 4 on the right side). In electroporation mode electrode 1 is pulsed against electrode 2, likewise electrode 3 is pulsed against electrode 4. In IPH mode, electrode 1 is connected to electrode 2 (with either positive or negative polarity) while electrode 3 is connected to electrode 4 with an opposite polarity; then electrodes 1 and 2 will be pulsed against electrodes 3 and 4. Of course, these operation parameters can be set or programmed into the minigenerator.

A vibration unit also can optionally be included in the apparatus, which can be used in combination with an electrical impulse to transdermally introduce a composition into the penis, if desired. A phonophoresis unit, which can transdermally introduce a composition into the skin by means of ultrasound, also can optionally be included in the apparatus, if desired. Thus, by applying vibration or ultrasound before, after or during pulsing and/or iontophoresis on the penile glans or midshaft, the composition can be driven deeper into the penis or a greater amount of the composition can be driven into the penis than pulsing alone. As above, a switching unit, such as an automated switch, optionally programmable, could be used to control the time between applying the impulse and applying vibration or ultrasound, as well as optionally controlling the time during which impulse, vibration or ultrasound is applied.

A means for administering a composition can optionally be included in the electrical apparatus, which can be used to administer the composition to the penis prior to, substantially contemporaneously with, or after applying an electric pulse, iontonophoresis, vibration or ultrasound, in their various embodiments. Depending on the specific formulation, a composition can be incorporated into a patch reservoir (e.g., as a nicotine patch), which is then attached both to the electrode and the penis. Formulations employed for IPH are advantageously used in this manner.

As used herein, the term "substantially contemporaneously" means that the electric pulse and the composition are applied to the penis reasonably close together in time. Preferably, the composition is administered prior to or concurrently with electropulsing. When applying multiple electrical impulses, the composition can be administered before or after each of the pulses, or at any time between the electrical pulses. When applying iontophoresis, vibration or ultrasound, the composition can be administered before or after each, and at any time between.

Restricting venous outflow from the penis can induce, enhance or maintain erectile function by maintaining the imbalance between arterial inflow and venous outflow, or by inhibiting outflow from the penis of a vasodilator or an androgenic composition transdermally introduced into the penis as set forth herein. Thus, a means for restricting venous flow from the penis optionally can be included in an invention apparatus as disclosed herein. For example, a mechanical constriction device, band, strap or clamp can be physically attached to the apparatus, such as the cuff, to be secured around the penis at the base (e.g., as with a tourniquet). Venous outflow can be controlled by varying the degree of penile constriction. The band or strap can be flexible or elastic (e.g., latex, butyl rubber, synthetic or natural elastomers etc.). Optionally, a tubular band of an appropriate thickness can be used to enable inflation of the tube band to adjust the degree constriction thereby controlling the amount of venous outflow from the penis. A bulb at one end of such a tube band having a closed opposing end can be used to apply pressure within the tube band thereby inflating the band; an optional pressure sensor can monitor the amount of pressure and a release valve or other appropriate pressure release mechanism can additionally be included to decrease or eliminate penile constriction when sufficient erection is attained or so as to not cause discomfort. The term "elastic" or "elasticity" as used herein refers to the ability of a solid material to change shape or size under opposing forces, to sustain such deformation without permanent loss of size or shape, and to recover most or all of its original configuration when the forces are removed. Preferred elastic bands or straps are flexible and capable of regaining their original shape after being deformed within their elastic limits; elasticity of a material can be quantified in a variety of ways, and can be modified by altering the composition. The band, strap, clamp etc. can be covered in fabric or otherwise modified to increase user comfort. Various flow control devices that can be used to control penile venous flow are known in the art and it is specifically contemplated that the invention electrical apparatus can be modified to incorporate such devices, if desired (see e.g., U.S. Pat. No. 5,855,548).

In addition to the various functional components that can be added to the invention electrical apparatus, each of the essential components of the invention apparatus can be modified, or can have additional functional components. For example, in the exemplary hand-held mini pulse generator/power source shown in FIG. 1, the pulse applicator 104 comprising the sheath is separable from the cuff 102, and the mini generator 100 is affixed to the cuff. However, the pulse applicator optionally can be affixed to the cuff, and the mini generator optionally can be separable from the cuff. Additionally, the nature of the electrode that can be used in the pulse applicator can be varied so long as it is capable of delivering a sufficient electric pulse as set forth herein. Thus, a variety of electrode types and configurations are contemplated in the invention apparatus.

In one embodiment, the electrode is a wire electrode (useful for in vitro studies, and the like). In another embodiment, the electrode is a plurality of electrodes (e.g., a micropatch electrode as described in U.S. patent application Ser. No. 09/134,245, filed on Aug. 14, 1998, which is hereby incorporated herein in its entirety by reference). In still yet another embodiment, the electrode comprises a meander electrode (e.g., an array of interweaving electrode fingers, with a typical electrode width in the range of about 0.2 up to about 1 mm, and an electrode gap of about 0.2 mm, wherein the gap can be filled with an electrically insulating substance). In an additional embodiment, the electrode is a porous electrode. The various electrodes used herein are preferably insulated to protect against excess heat or burning, current leakage, shock, etc. Appropriate electric pulsing parameters are set forth herein or can be determined using the teachings herein and, in view of these parameters, the skilled artisan can select among various suitable electrode types (e.g., ceramic, metal, etc.) and configurations (single wire, multiple wire, etc.) available in the art.

The cuff can be manufactured of essentially any material compatible with applying an electrical impulse to the penis. The cuff can be made of a single material type or can be made of multiple material types. In one embodiment, the cuff is manufactured of a single flexible cushioned or compressible material. In another embodiment, the inner cuff, which contacts the penis, is made of a cushioned or compressible material and the outer cuff is made of a rigid material, such as plastic, metal, an alloy, or a combination thereof. Although the cuff of the exemplified apparatus has a relatively fixed size, preferably the cuff is adjustable or compressible so as to accommodate various penis sizes and different states of penile tumescence. For example, in one embodiment, the apparatus has an inner cuff separable from an outer cuff, and has variously sized inner cuff pieces (e.g, different thickness), optionally compressible, that can be inserted into the outer cuff so as to be adjustable with respect to cuff size. Preferably, the various cuff embodiments of the invention apparatus are hypo-allergenic, non-allergenic or so modified to be non-allergenic.

Figure 14:
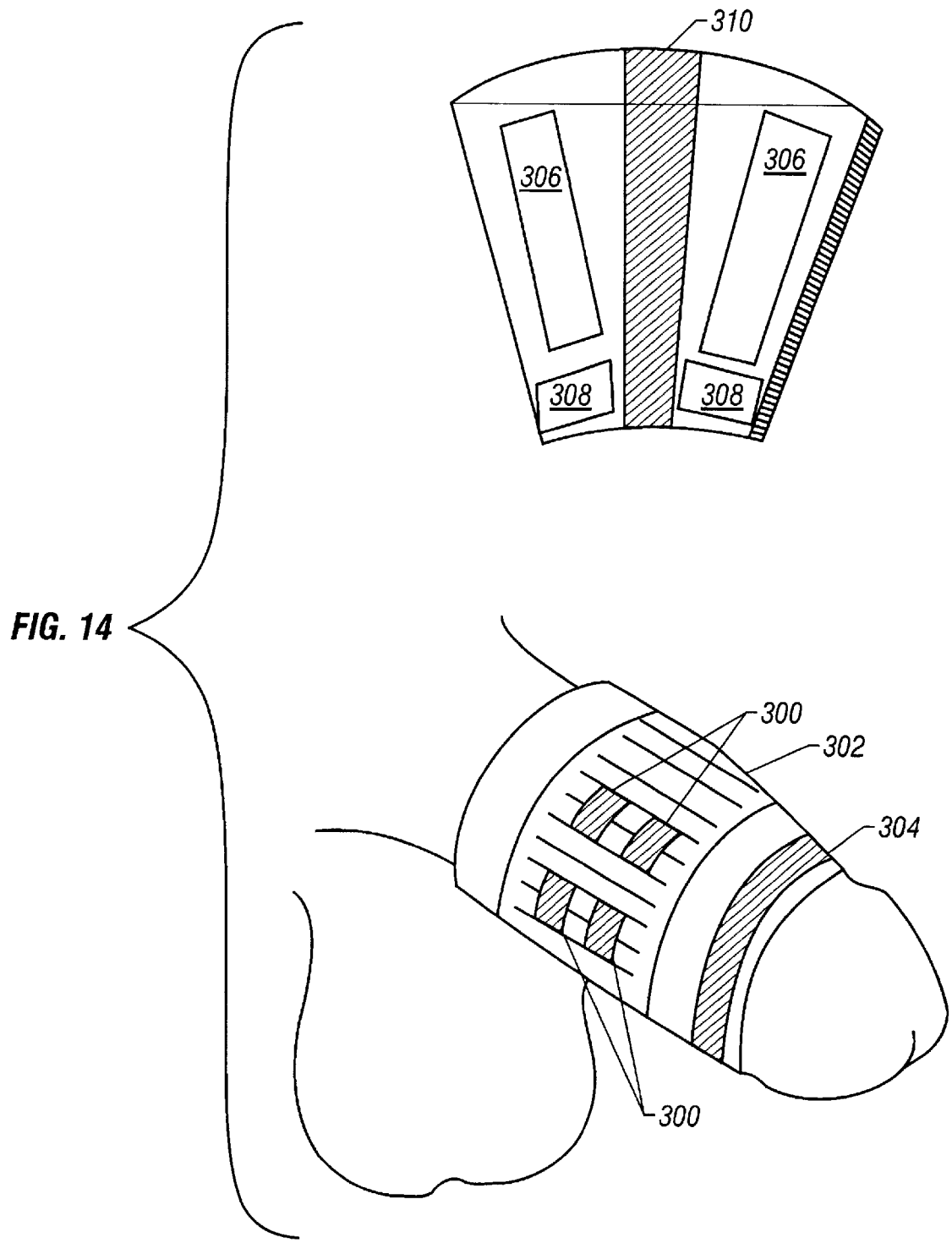
FIG. 14 shows an exemplary transdermal delivery system for ED (open-condom type device with all function units) in the unwrapped conformation and as worn (depicting color bands showing patients the location of electrodes).

The invention apparatus can have an indicating means to ensure proper positioning of the apparatus relative to the penis. For example, a visible band on the apparatus can indicate where the apparatus should be located relative to the shaft and/or glans. A visible band additionally can indicate proper penile location relative to the electrodes used for applying the pulse to the penis. For example, referring to FIG. 14, two differently colored bands 302 and 304, each of which indicate the electrodes for the shaft and for the glans respectively, can be included. Alternatively, the apparatus can be modified or manufactured to have sufficient transluscence (e.g., clear polycarbonate) so that the penis can be visualized in order to achieve proper positioning. In another alternative, a "closed condom" or "cone" shaped apparatus can be manufactured such that inserting the penis all the way to the end of the cone ensures proper positioning within the apparatus (See, e.g., FIG. 14 showing the open condom embodiment, as worn, and as viewed from the inside in an opened view).

Figure 2:
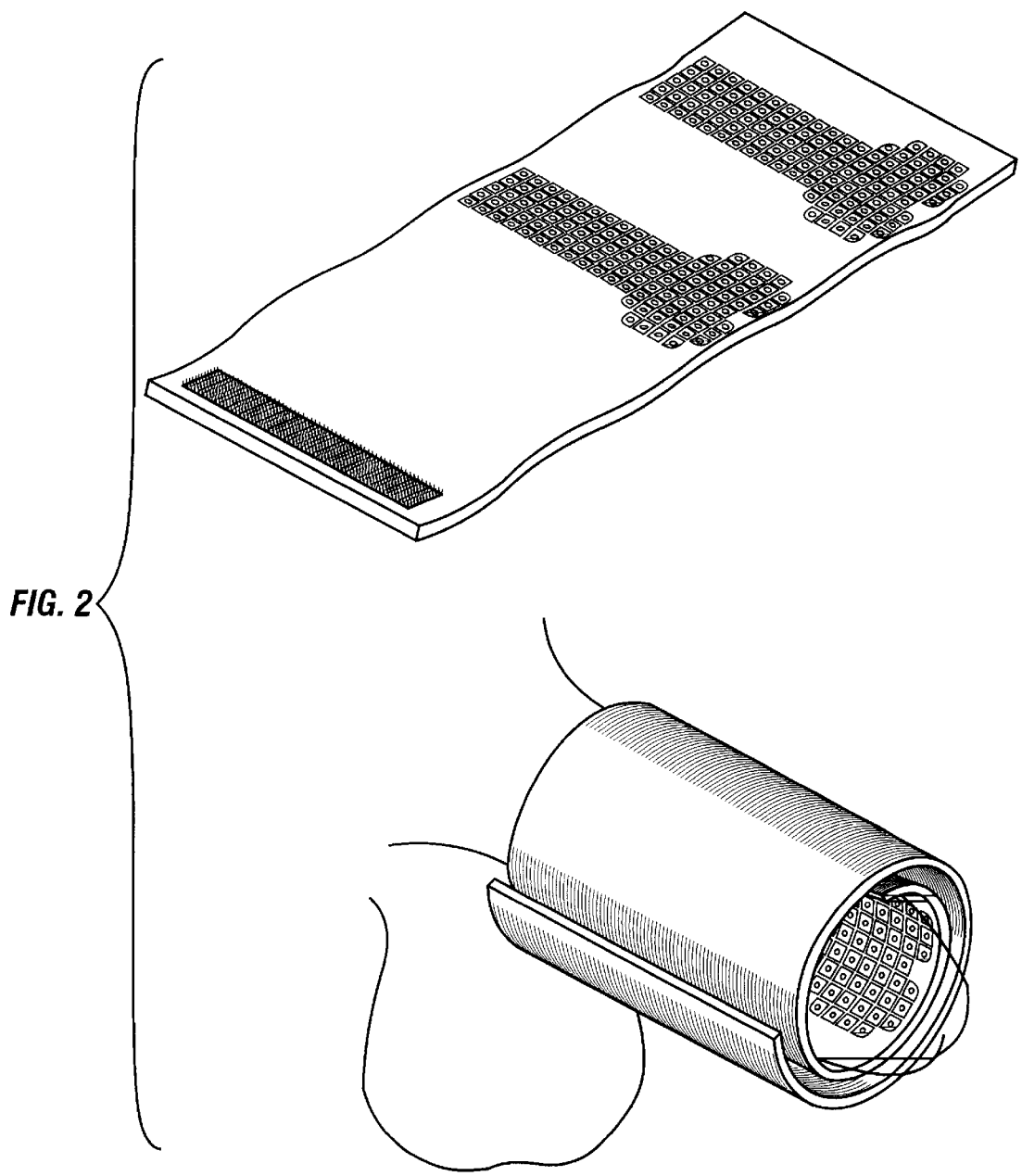
FIG. 2 shows an exemplary pulse applicator with incorporated electrodes and having a VELCRO™ fastening means for use in the electrical apparatus of FIG. 1.

Mere pressure, such as that provided by hand, can be sufficient to secure the invention electrical apparatus about the penis. Alternatively, a fastening means, optionally adjustable, can be used for securing the electrical apparatus. For example, the exemplified apparatus has a snap-closure fastening means attached thereto (e.g., the cuff, FIG. 1). Additional contemplated fastening means include, for example, VELCRO, snap, buckle, clip, clamp, adhesive tape and coupling mechanism. An adjustable fastening means has the advantage of being able to accommodate various penis sizes and different states of penile tumescence as well as exerting pressure on the penis to drive more of the composition into the penis, or drive the composition into deeper areas of the penis. Alternatively or in addition, the pulse applicator, if desired, can be modified to include a fastening means as described herein. In a particular aspect, a pulse applicator fastening means is VELCRO™ (FIG. 2).

As described herein, the separable pulse applicators optionally are disposable. Thus, in accordance with the present invention, a kit comprising at least one pulse applicator is further provided. The kit contains appropriate packaging material and instructions relevant to the enclosed pulse applicator. Preferably, the pulse applicator has been sterilely manufactured or treated to be sterile and packaged to maintain sterility. In addition to the above described components, the kit optionally contains one or more androgenic or vasoactive compositions, such as those described herein or known in the art, for use with the enclosed pulse applicator in the electrical apparatus.

The invention apparatus can have a variety of other "user friendly" functionalities in addition to the optional controlling means ("activator button") for applying an electric pulse, indicating means and fastening means. For example, the apparatus can have an indicating means for indicating apparatus ready, the various pulse parameter settings (e.g., voltage, capacitance, pulse duration, time delay between pulses, pulse wave type), pulse(s) applied, parameters of the applied pulse(s) (e.g., voltage, capacitance, pulse duration, pulse wave type, number of pulses) or a combination thereof. Such indicating means can be visual, audible, or a combination thereof. For example, a single audible "beep" can indicate that the "apparatus is ready," two audible "beeps" can indicate that a pulse has been correctly applied and three audible "beeps" can indicate a malfunction or that the pulse was not or was improperly applied. Visual indicating means include analog or digital alpha-numeric displays (e.g., LCD, LED and the like), as in watches, and further can include illuminating means for low light visualization, for example, by white light, electroluminescent backlighting for LCD or electroluminescent lamps (i.e. INDIGLO™), or by various fluorescent or radioactive illuminating compositions, and the like.

Additional "user friendly" functions include the aforementioned controlling means for applying an electric pulse (e.g., pushbutton, knob, lever switch, dial and the like) as well as means for adjusting parameters (e.g., pushbutton, knob, lever switch, dial and the like) including, for example, pulse duration, voltage, capacitance, field strength, number, wave type and penile location (e.g., one or both sides of the midshaft or shaft, the glans, or a combination thereof). Means for adjusting, setting, storing or retrieving one or more pulse parameters also are included herein. Such means include traditional mechanical electronic controls (e.g., a selector switch controlling each parameter in which the switch has a plurality of settings; exemplary pulse length settings, 5 msec, 10 msec, 25 msec, 35 msec, 50 msec, for example.) as well as a chip control (e.g., silicon wafer types commonly used in the computer industry) which is controlled, for example, by a pushbutton interface, as in watches for example. A chip, optionally removable from the apparatus or, user and/or manufacturer programmable for control of the various pulse parameters set forth herein also is contemplated. Storage capacity of such a chip is sufficient to provide virtually unlimited fine control of the various parameters, as well as storing different pulse parameter settings for different compositions, users and the like. As each of the various electronic functionalities of the invention apparatus described herein can be controlled or managed by a computer chip, a chip affords the option of additionally incorporating software, if desired, said software optionally user programmable.

In addition to efficacy, both sensation and user safety are important. Thus, in another embodiment, the invention further provides an apparatus having means for preventing applying excess pulse voltage, duration, field strength and/or number. Any means which passively or actively interrupts or disrupts the electric circuit, including fuses, circuit breaker switches, and the like, or devices that actively monitor the various pulse parameters and interrupt or disrupt the electric circuit to prevent excess pulse voltage, duration, field strength, pulse number from being applied can be incorporated into the circuit path. Those skilled in the art of electrical devices will know of other protective elements that prevent applying excess pulse voltage, duration, field strength or number.

The electric pulse can be provided by any electronic device that provides an appropriate electric pulse or electric source sufficient for transdermally introducing a composition into the penis. Suitable electric pulses for transdermally introducing compositions into the penis therefore include, for example, square wave pulses, exponential waves, unipolar oscillating wave forms, bipolar oscillating wave forms, other wave forms generating electric fields, or a combination of any of these forms. Each pulse wave form has particular advantages; square wave form pulses provide increased efficiencies in transporting compounds into the cells in comparison to exponential decay wave form pulses, and the ease of optimization over a broad range of voltages, for example (Saunders, "Guide to Electroporation and Electrofusion," 1991, pp. 227–47). Preferably, the waveform used is an exponential or a square wave pulse.

An exemplary electric impulse for transdermally introducing a composition into the penis is a pulsed electric field, such as that provided by an electroporation apparatus. Exemplary pulse generators capable of generating a pulsed electric field include, for example, the ECM600, which can generate an exponential wave form, and the ElectroSquare-Porator (T820), which can generate a square wave form, both of which are available from BTX, a division of Genetronics, Inc. (San Diego, Calif.). Additional electroporation type apparatus are commercially available and can be used to generate the pulse for the invention apparatus and in practicing the invention methods. Such pulse generators can be operatively connected to the pulse applicator as shown in FIG. 3, for example, or alternatively can be physically connected to the cuff or pulse applicator. A pulse generator, physically connected, is preferably portable or lightweight, as in the exemplary mini- pulse generator 100 (FIG. 1), and an optional portable DC power source, such as batteries, optionally being rechargeable, can be included to provide the power source to the pulse generator.

The results showing that an electrical impulse applied to the penis transdermally introduces topically applied PGE1 or trimix (papavarine, phentolamine and PGE1) into the penis thereby inducing or enhancing erectile function are shown in Examples I to III and in FIGS. 4 to 8. Exemplary pulse parameters for transdermally introducing a composition into rabbit penis, human skin and human penile skin are described herein in Examples I to IV.

Thus, in accordance with the present invention, methods for delivering a composition into the penis of a subject are provided. In one embodiment, the method comprises applying an electric pulse to the penis substantially contemporaneously with a composition, in which the electric pulse has sufficient strength and duration for transdermally introducing the composition into the penis in an amount greater than passive diffusion.

In another embodiment, methods for treating erectile dysfunction or for inducing, enhancing or maintaining erectile function in a subject are provided. A method comprises applying an electric pulse to the penis substantially contemporaneously with a vasoactive or androgenic composition of sufficient strength and duration for transdermally introducing an effective amount of the composition into the penis, thereby treating erectile dysfunction or inducing, enhancing or maintaining erectile function.

As the invention methods for treating erectile dysfunction or for inducing, enhancing or maintaining erectile function also prevent or inhibit impotence, the invention further provides methods for preventing or inhibiting impotence in a subject. The method comprises applying an electric pulse to the penis substantially contemporaneously with a vasoactive or androgenic composition, said electric pulse having sufficient strength and duration for transdermally introducing an effective amount of the composition into the penis for preventing or inhibiting impotence. The methods for preventing or inhibiting impotence in a subject can be modified as described herein as with the various embodiments of the methods for treating erectile dysfunction or for inducing, enhancing or maintaining erectile function.

In one aspect, the electric pulse is applied to the penile glans. In another aspect, the electric pulse is applied to one side of the penile shaft. In various other aspects, the pulse is applied to both sides of the shaft, either side of the midshaft, both sides of the midshaft and both the penile glans and the midshaft.

Generally, the pulse strength applied to the penis will range from about 25 to about 200 volts, preferably from about 40 to about 100 volts and more preferably from about 50 to about 80 volts. The pulse duration generally will be from about 100 microseconds ($\mu$s) to 100 milliseconds (ms), preferably from about 500 $\mu$s to about 50 ms and more preferably from about 1 ms to 30 ms. The capacitance will generally range from about 100 to about 1000 $\mu$F, preferably from about 200 to about 800 $\mu$F, more preferably from about 400 to about 1000 $\mu$F. There can be from about 1 to about 25 pulses applied. Preferably, the number of pulses is from about 1 to about 10 pulses and more preferably from about 1 to about 6 pulses per cycle. Most preferably, 5 to 15 pulse cycles are applied.

The voltage, waveform type, pulse duration, capacitance, field strength and the number of pulses applied will vary depending on the location of the pulse and the nature of the composition to be transdermally introduced. For example, as the glans is more sensitive than the shaft, low voltage and short pulses, preferably in combination with iontophoresis, is preferred on the glans. The glans is less electrically resistant than the shaft and therefore, less voltage may be needed to transdermally introduce compositions into the glans. For the shaft, relatively higher voltages and longer pulses are tolerable. Particular electrical parameters for transdermally introducing a composition into the penis, other than those exemplfied herein, can be empirically determined if necessary, in view of the teachings herein and of the general knowledge of those having skill in the art, for example, relating to the electroporation of mammalian cells in vivo.

The terms "androgenic" or "vasoactive" composition refers to a drug, agent, compound or chemical that has or that can produce or enhance one or more activities characterized as "androgenic" or "vasoactive" as is known in the art. When administered to a subject, such compositions induce or enhance an "androgenic" or "vasoactive" effect. As used herein, a "vasoactive composition" means a substance having the capability of altering the physiologic state, especially the tone and diameter, of a vessel. Thus, a "vasodilator" is a composition that induces or enhances vessel relaxation or dilation and a "vasoconstrictor " is a composition that induces or enhances vessel rigidity or constriction. As used herein, an "androgenic composition" refers to a substance having or capable of enhancing an erection. Various androgenic and vasodilating drugs and other compositions having such properties are described herein and are further known to those skilled in the art and as such are applicable in using the invention apparatus and in practicing the invention methods.

Although not wishing to be bound by any theory, it is believed that the common channels for the drainage of the glans, corpus spongiosum, and the corpus cavernosum are the route for drug transfer from the spongiosal to the cavernosal compartment (Vardi et al., Urology vol. 49 (1997)). Thus, in all likelihood, the compositions transdermally introduced into the penis for treating erectile dysfunction or for inducing, enhancing or maintaining erectile function are driven into the corpus cavernosum or into the blood vessels that supply the corpuscavernosum thereby producing a local effect or function within the erectile tissue.

As used herein, the term "local," when used in reference to a composition, refers to its function in a particular region. Thus, a vasoactive composition transdermally introduced into the penis is believed to exert its vasoactive function within the penis. Nevertheless, the skilled artisan will recognize that some transdermally introduced compositions may have a systemic effect or function, such that after transdermally introducing the composition into the penis, the composition is distributed to other areas of the subject thereby producing or contributing to treating erectile dysfunction or inducing, enhancing or maintaining erectile function by acting at a site other than the penis. As used herein, the term "systemic," when used in reference to a composition, means that the composition functions outside the penis. It is specifically contemplated that compositions that function systemically are included herein in addition to those functioning locally or both systemically and locally.

Any composition can be used in the methods of the invention, so long as the composition, when transdermally introduced into the penis, is capable of treating erectile dysfunction or inducing, enhancing or maintaining erectile function, as set forth herein. Compositions contemplated for use include drugs (e.g., vessel vasodilators and androgenic compositions), polynucleotides (e.g., genes used in gene therapy, for example, those that are involved in the erectile function biochemical pathways or those that encode vasoactive or androgenic polypeptides or fragments thereof; antisense nucleotides to vasoconstrictor polypeptide including RNAi antisense; ribozymes), polypeptides (e.g., vasoactive peptides and proteins, functional derivatives thereof including, for example, protease resistant analogs). Modified compositions that are biologically functional analogs or derivatives of the compositions described herein (salts, esters etc.) also are useful in the methods of the invention (see also e.g., Trampota et al., U.S. Pat. No. 5,618,959, which describes various $PGE_1$ and $PGE_2$ analogs and derivatives).

Specific vasoactive compositions include, for example, prazosin and papeverine; naturally occurring protaglandins, $PGE_1$, $PGE_2$, $PGE_1$, $PGA_1$, $PGB_1$, $PGF_1$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$, $PGI_1$, $PGI_2$; prostaglandin derivatives, carboprost tromethamine, dinoprost tromethamine, dinoprostone, lipoprost, gemeprost, metenoprost, sulprostone, tiaprost; nitric oxide releasing agents, nitroglycerin, isosorbide dinitrate, erythrityl tetranitrate, amyl nitrate, sodium nitroprusside, molsidomine, (Z)-1-{N-methyl-N-[6-(N-methyl-ammoniohexyl)amino]}diazen-1-ium-1,2-diolate (MAHMA/NO), (Z)-1-[N-(3-ammoniopropyl)-N-(n-propyl)amino]diazen-1-ium-1,2-diolate (PAPA/NO),(Z)-1-{N-[3-aminopropyl]-N-[4-(3-aminopropylammonio) butyl]-amino}diazen-1-ium-1,2-diolate (SPER/NO), sodium (Z)-1-(N,N-diethylamino)diazenium-1,2-diolate (DEA/NO), linsidomine (SIN-1), S-nitrosothiols, S-nitroso-N-acetyl-D,L-penicillamine (SNAP), S-nitroso-N-cysteine and S-nitroso-N-glutathione (SNO-GLU); vasoactive intestinal peptide agonists and derivatives thereof; smooth muscle relaxants; leukotriene inhibitors; calcium channel blockers; α1-adrenergic antagonists; α2-adrenergic agonists; phosphodiesterase inhibitors; antihypertensive agents such as angiotensin-converting enzyme (ACE) inhibitors and angiotensin II receptor antagonists; phenoxybenzamine, dibenamine, doxazosin, terazosin, phentolamine, tolazoline, prazosin, trimazosin, alfuzosin, indoramin, ergotamine analogs, ergotamine analogs, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride, diazoxide, hydralazine and minoxidil, nimodepine, pinacidil, cyclandelate, dipyridamole, isoxsuprine, chlorpromazine, haloperidol, yohimbine, trazodone; dopamine antagonists such as apomorphine and bromocriptine; and opioid antagonists such as naltrexone. Other vasoactive compositions which can be appropriate for use may be found, for example, in Remington's Pharmaceutical Sciences, 18th ed., Mack Publishing Co., Easton, Pa., 1990; The Merck Index, 12th ed., Merck Publishing Group, Merck & Co., Inc., Whitehouse, N.J., 1996; and 51st ed. Physicians Desk Reference, Medical Economics Data Co., Montvale, N.J., 1997, which are herein incorporated by reference.

Suitable androgenic compositions include, for example, androsterone, testosterone, dihydrotestosterone, testosterone analogs such as dehydroepiandrosterone (DHEA) and DHEA sulfate, enanthate, propionate, cypionate esters of testosterone, phenylacetate esters of testosterone, testosterone alkyls, methyltestosterone, testolactone, oxymetholone and fluoxymesterone. Other androgenic compositions which may be appropriate for use can be found, for example, in Remington's Pharmaceutical Sciences, supra; 1997 Physicians Desk Reference, supra; and The Merck Index, 12th ed., supra.

The compositions used with the invention electrical apparatus and in the invention methods will be transdermally introduced into the penis in an amount effective to produce a desired therapeutic effect, i.e., an amount sufficient to induce, enhance or maintain an erection sufficient for sexual intercourse. As used herein, the term "effective" means an amount of drug or pharmacologically active agent that is sufficient to provide the desired effect (e.g., an androgenic or vasoactive effect) in which the signs or symptoms of the clinical situation are ameliorated (e.g., sufficient erectile dysfunction is ameliorated so as to enable sexual intercourse). The amount should not be so large as to cause excessive adverse side effects, such as skin irratation, burning or tissue damage. The amount required will vary from subject to subject, depending on the species, age, and general condition of the subject (physiological and psychological), the severity of the condition being treated (e.g., chronic vs. acute erectile dysfunction), the drug or agent being employed, the mode of administration (e.g., if an oral drug such as VIAGRA is co-administered in conjunction with electropulsing, less vasoactive or androgenic composition may be required; the alternative also is true), etc. Thus, although it is not possible to specify an exact "effective amount," an appropriate "effective" amount in any individual case may be determined by one of ordinary skill in the art using the teachings herein. For example, by visual inspection or by measuring penile hemodynamic parameters in response to various amounts of the composition, an effectivew amount can be readily determined. The amount can be adjusted by the individual or, in the event of any complication, by the physician.

The compositions used in a method of the invention are preferably administered by topical application to the penile skin. The term "topical" is used herein to refer to administration of a composition on the surface of the skin or mucosa which can be applied via direct application (i.e. spreading), via a drug impregnated skin patch (as in the nicotine patch, for example), or by an aerosol or other misting device, for example. Other modes of administration also are included, for example, by injection intravenously, intraperitoneally, intramuscularly, subcutaneously, intracavity, etc. Compositions also can be administered into the urethra, for example, with a suppository or urethral cathete having at least one port for introducing the composition into the urethra.

Androgenic and vasoactive compositions, when administered in a method of the invention, will generally be in "pharmaceutically acceptable" or "physiologically acceptable" formulations for therapeutic use. As used herein, the terms "pharmaceutically acceptable" and "physiologically acceptable" refer to carriers, diluents, excipients and the like that can be administered to a subject, preferably without excessive adverse side effects (e.g., for a topically applied formulation, skin rash, irritation, etc.). Particular formulations include aqueous or non-aqueous solutions, suspensions, emulsions, waxes, creams, lotions, oils or other liquid and cosmetic formulations suitable for topical application known in the art. Such formulations are or can be made compatible with applying an electrical impulse,. For example, the conductivity should not be too high to produce heat or electrical arching or too low to provide resistance thereby inhibiting delivery of the pulse to the skin. Examples of non-aqueous solvents are propylene glycol, polyethylene glycol (PEG) in its various molecular weights (e.g., PEG 400, PEG 400 monostearate, PEG 4000 etc.), glycerine, polyvinyl pyrrolidine (PVP), polyvinyl alcohol (PVA), mannitol, vegetable oils such as olive oil, and injectable organic esters such as ethyl oleate, and the like. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives, surfactants and other additives may also be present such as, for example, antimicrobial, anti-oxidants (e.g., BHT, BHA), chelating agents (e.g. EDTA, EGTA), and inert gases and the like. It is also possible to entrap a vasoactive or androgenic composition into micro-capsules prepared by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, and lipid-based systems including oil-in-water emulsions, micelles, mixed micelles, and liposomes (e.g., stabilized liposome formulations of vasoactive intestinal peptide). The preparation of an appropriate pharmaceutical formulation for therapeutic use is well within the general knowledge in the art (see e.g., Remington's Pharmaceutical Sciences, supra; 1997)

The above-described compositions and others not specifically described herein are useful in various clinical situations and can be administered alone, or in a combination with other compositions by a method of the invention. Combining low dose of oral pills with electropulsing can provide an additive or synergistic effect in the methods for treating erectile dysfunction or for inducing, enhancing or maintaining erectile function while minimizing some of the side effects of oral therapy and are therefore specifically included. An additive or synergistic effect also can be produced by administering a vasoactive or androgenic composition to the subject by injection or transurethrally in another embodiment. Vacuum treatment and/or topical cream can be employed with electrostimulation.

Accordingly, in another embodiment, the invention provides a method for treating erectile dysfunction or for inducing, enhancing or maintaining erectile function by applying an electric impulse having sufficient strength and duration for transdermally introducing an effective amount of a vasoactive or androgenic composition into the erectile tissue in combination with administering a vasoactive or androgenic composition orally, by injection or transurethrally, or topical cream or vacuum, thereby treating erectile dysfunction or inducing, enhancing or maintaining erectile function.

In addition, electrically-induced transdermal introduction of a vasoactive or androgenic composition into the penis can be increased over that of electropulsing alone by a variety of other means. For example, applying pressure on glans or midshaft can provide an additional driving force to transport drug into the glans and cross tunica albuginia, or into the midshaft. Restricting venous flow from the penis by applying a contriction at the base of penis prior to or after electropulsation using a penile rubber band, for example, can prevent penile venous flow while medication is administered and subsequently result in a better degree and duration of erection.

Applying iontophoresis of the glans, midshaft or both, before or after electropulsing the glans, midshaft or both, can augment electrically induced transdermal introduction of a vasoactive or androgenic composition. Similarly, applying vibration or phonophoresis to the glans or midshaft or both prior to or after electropulsing can drive medications into deeper layers of the penis, such as into the spongiosum or tunica albuginia. Alone, or in any combination, these additional techniques can be used in conjunction with electropulsing to transdermally introduce a composition into the penis (e.g., electropulsing with iontophoresis, restricting venous flow or vibration; electropulsing with iontophoresis and restricting venous flow, and so forth).

A "permeation enhancer" also can be included with electropulsing to increase transdermal introduction of a composition into the penis. As used herein, the term "permeation enhancer" refers to any action (e.g., mechanical, physical, chemical) or any composition that can increase or "augment" transdermally introducing a composition into the penis. The term "augment," when used herein as a modifier of transdermal introduction, means that the rate (over time) or amount of composition transdermally introduced into the penis via electropulsing is greater than that produced by electropulsing in the absence of the permeation enhancer. Thus, administering a permeation enhancer prior to, substantially contemporaneously with or after applying a vasoactive or androgenic composition to the penis may "augment" electrically induced transdermal introduction of the composition into the penis. Alternatively, a permeation enhancer can be mixed with the composition in the pharmaceutical formulation to be transdermally introduced. Permeation enhancer compositions that increase skin permeability include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate, and the like. Permeation enhancers further include mechanical or physical actions that function in association with an electrical impulse (i.e., generally require applying an electrical pulse to augment transdermal introduction of the compositions into the penis; e.g., vibration).

The following examples are intended to illustrate but not limit the invention. While they are typical of those that might be used, other procedures and applications of the invention methods known to those skilled in the art may alternatively be used.

EXAMPLE I

This example describes initial studies of topical application of PGE1 on the penile glans, shaft or both of rabbits followed by application of a pulsed electric field, and the change in intracavernosal pressure associated with penile erection produced in response. Although rabbits were used in these studies, dogs, cats, and monkeys are also useful animal models for use in research.

Three New Zealand White rabbits (n=3) weighing between 3–3.5 kg were used for these studies. Briefly, various concentrations of PGE1 were topically applied to the penis (shaft, glans or both) of rabbits anesthetized with intravenous administration of sodium pentobarbital. The electric pulse was applied by a meander electrode placed around the penis connected to a BTX 600 pulse generator (Genetronics, Inc., San Diego, Calif.). Carotid artery was dissected for on-line measurement of systemic arterial pressure. A 21 gauge minicatheter was inserted intracavernosally for measurement of intracavernosal pressure. To ensure erectile potency, rabbits #2 and #3 were intracavernosally injected with papaverine and phentolamine injection, which caused a full penile erection in both rabbits. The procedures performed on the glans penis or on the penile shaft while recording systemic blood pressure and intracavernosal pressure are as follows:

1. Application of electric pulse alone (without PGE1).
2. Topical application of PGE1 alone (without electrical pulse).
3. Topical application of PGE1 in conjunction with electric pulse.

Rabbit #1

Pulse stimulation alone at 13 ohm, 800 $\mu$F and 90V on glans penis did not affect arterial blood pressure while causing a decrease in intracavernosal pressure from 25 mm Hg to 10 mm Hg. As those of skill in the art will understand, the resistance can be multiplied by the capacitance and the result divided by one thousand to give the pulse time in milliseconds. PGE1 (1 mg/20 $\mu$l or 5 mg/20 $\mu$l) alone on glans penis did not affect arterial or intracavernosal pressure. PGE1 (1 mg/20 $\mu$l) on glans penis and pulse stimulation on glans penis at 13 OHM, 800 $\mu$F and 90V caused a slight increase in arterial pressure while causing a decrease in intracavernosal pressure from 28 mm Hg to 10 mm Hg. PGE1 (5 mg/20 $\mu$l) on glans penis and pulse stimulation on glans penis at 13 OHM, 400 $\mu$F and 60V did not affect arterial pressure while causing an increase in intracavernosal pressure from 18 mm Hg to 32 mm Hg. Response duration was 96 seconds. A second pulse stimulation at 13 OHM, 400 $\mu$F and 60V with the same concentration of PGE1 (5 mg/20 $\mu$l) on the glans caused an increase in intracavernosal pressure from 20 mm Hg to 32 mm Hg. Response duration was 115 seconds.

Rabbit #2

Pulse stimulation alone at 13 OHM, 400 $\mu$F and 60V on glans penis did not affect arterial blood pressure or intracavernosal pressure. PGE1 (10 mg/20 $\mu$l) alone on glans penis did not affect arterial or intracavernosal pressure. PGE1 (10 mg/20 $\mu$l) on glans penis and pulse stimulation on glans penis at 13 OHM, 400 $\mu$F and 60V did not affect arterial pressure while increasing intracavernosal pressure from 15 mm Hg to 27 mm Hg. Response duration was 1 minute. A second pulse stimulation at 13 OHM, 400 $\mu$F and 60V in the presence of an additional 2 mg PGE1 on glans penis caused an increase in intracavernosal pressure from 22 mm Hg to 32 mm Hg. Response duration was 95 seconds.

Pulse stimulation alone at 13 OHM, 400 $\mu$F and 60V on penile shaft did not affect arterial blood pressure or intracavernosal pressure. PGE1 (5 mg/20 $\mu$l) alone on penile shaft did not affect arterial or intracavernosal pressure. PGE1 (5 mg/20 $\mu$l) on penile shaft and pulse stimulation on penile shaft at 13 OHM, 400 $\mu$F and 70V did not affect arterial pressure while causing an increase in intracavernosal pressure from 20 mm Hg to 28 mm Hg. Response duration was 32 seconds. A second pulse stimulation at 13 OHM, 400 $\mu$F and 60V on penile shaft caused an increase in intracavernosal pressure from 26 mm Hg to 37 mm Hg. Response duration was 45 seconds.

Rabbit #3

Pulse stimulation alone at 13 OHM, 400 $\mu$F and 60V on glans penis did not affect arterial blood pressure or intracavernosal pressure. PGE1 (5 mg/20 $\mu$l) alone on glans penis did not affect arterial or intracavernosal pressure. PGE1 (5 mg/20 $\mu$l) on glans penis and pulse stimulation on glans penis at 13 OHM, 400 $\mu$F and 60V did not affect arterial pressure while causing only a minor increase (5 mm Hg) in intracavernosal pressure. A second pulse stimulation at 13 OHM, 400 $\mu$F and 60V on glans penis in the presence of an additional 5 mg PGE1 on the glans increased intracavernosal pressure from 15 mm Hg to 23 mm Hg. Response duration was 30 seconds.

PGE1 (10 mg/20 $\mu$l) on glans penis and pulse stimulation on glans penis at 13 OHM, 400 $\mu$F and 50V did not affect arterial pressure while causing only a minor increase (7 mm Hg) in intracavernosal pressure. PGE1 (10 mg/20 $\mu$l) on glans penis and pulse stimulation on glans penis at 13 OHM, 200 $\mu$F and 50V did not affect arterial pressure but increased intracavernosal pressure from 15 mm Hg to 20 mm Hg. A second pulse stimulation at 13 OHM, 150 $\mu$F and 50V on glans penis in the presence of an additional 2 mg PGE1 on glans increased intracavernosal pressure from 15 mm Hg to 22 mm Hg. Response duration was 45 seconds.

Pulse stimulation alone at 13 OHM, 150 $\mu$F and 50V on penile shaft did not affect arterial blood pressure on intracavernosal pressure. PGE1 (5 mg/20 $\mu$l) alone on penile shaft did not affect arterial or intracavernosal pressure. PGE1 (5 mg/20 $\mu$l) on penile shaft and pulse stimulation on penile shaft at 13 OHM, 150 $\mu$F and 50V did not affect arterial or intracavernosal pressure. A second pulse stimulation at 13 OHM, 400 $\mu$F and 60V on penile shaft in the presence of an additional 5 mg PGE1 on penile shaft did not affect arterial or intracavernosal pressure. A third pulse stimulation at 13 OHM, 400 $\mu$F and 60V in the presence of an additional 5 mg PGE1 on the penile shaft did not affect arterial or intracavernosal pressure.

Figures 4A, 4B:
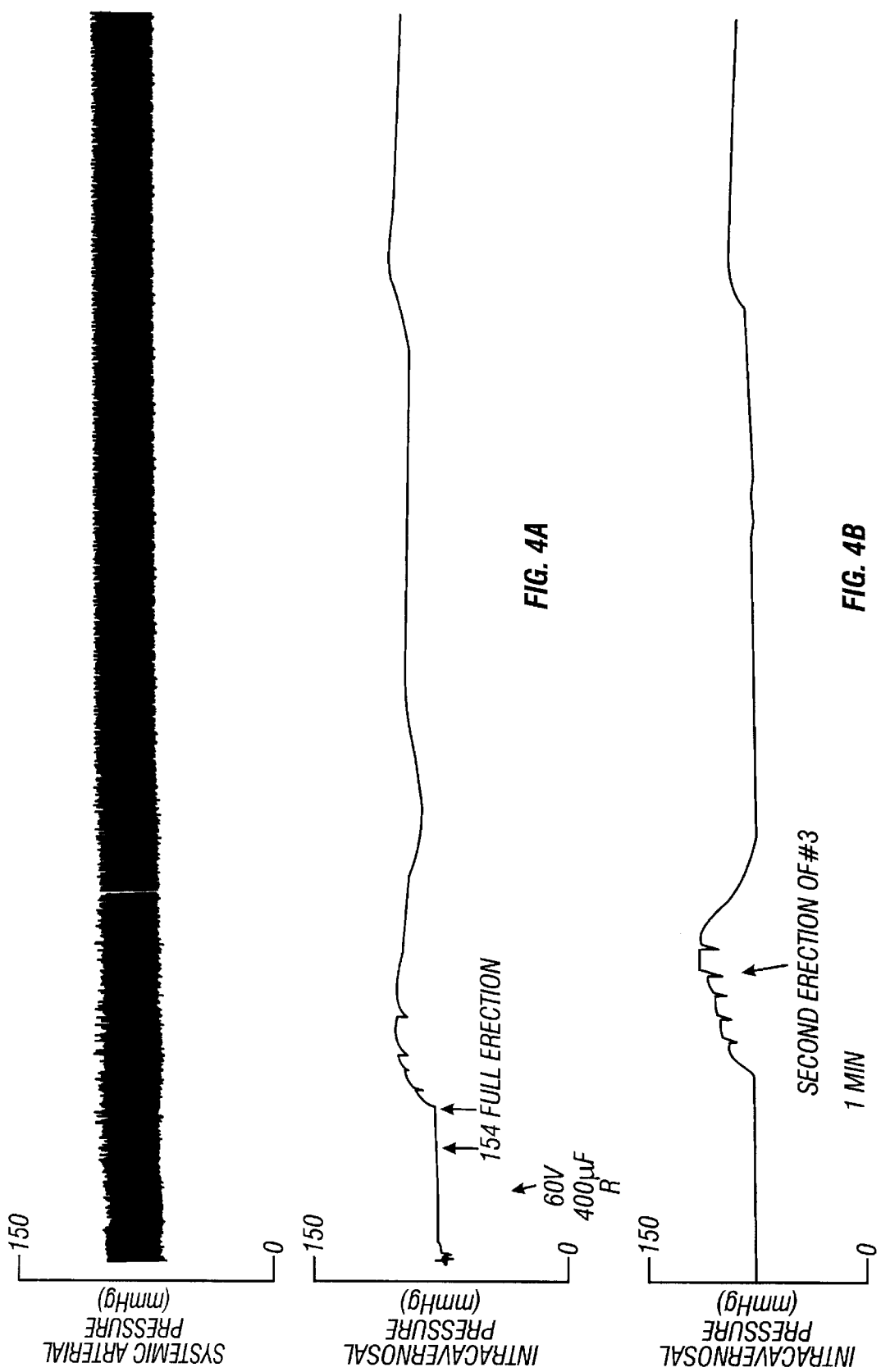
FIGS. 4A and 4B show the arterial (upper horizontal line) and penile intracavernosal pressure (lower horizontal line) in a rabbit in which PGE1 (10 mg/20 µl) was applied to the glans penis and to the penile shaft and a first electric pulse (of 5.2 ms and 60V) applied to the glans penis and shaft (pulse indicated by arrow) produced a sharp increase in intracavernosal pressure resulting in a full erection (A). After 22 minutes and spontaneous detumescence, an additional 10 mg PGE1 was applied to the glans and shaft and a second electric pulse (of 5.2 ms and 60 V) applied to the glans and shaft produced a sharp increase in intracavernosal pressure resulting in a full penile erection lasting for 15 minutes (B). Neither the first nor the second pulse affected arterial pressure.

PGE1 (10 mg/20 $\mu$l) on glans penis and penile shaft and pulse stimulation on glans penis and penile shaft at 13 OHM, 400 $\mu$F and 60V did not affect arterial pressure while causing a remarkable increase in intracavernosal pressure. With this concentration of PGE1 and stimulation on the glans and shaft, intracavernosal pressure increased from 17 mm Hg to 48 mm Hg, resulting in a full erection (FIG. 4A). After 22 minutes there was a spontaneous detumescence. A second pulse stimulation at 13 OHM, 400 µF and 60 V on the glans and shaft in the presence of an additional 10 mg PGE1 on the glans and shaft caused an increase in intracavernosal pressure from 17 mm Hg to 48 mm Hg, resulting in full penile erection lasting for 15 minutes (FIG. 4B).

EXAMPLE II

This example shows that topical application of PGE1 or trimix (papavarine, phentolamine and PGE1) on the penile glans, shaft or both followed by application of a pulsed electric field induced penile erection in rabbits.

New Zealand White rabbits (n=6) weighing between 3–3.5 kg were studied for studies the effect of topical PGE1 crystals, topical trimix and pulsed electrical field stimulation on penile erection. The concentration of PGE1 for each topical application was 10 mg/100 µl. The concentration of trimix for each topical application was 10 mg papavarine+ 0.5 mg phentolamine+0.2 mg PGE1 in 100 µl.

Figure 7:
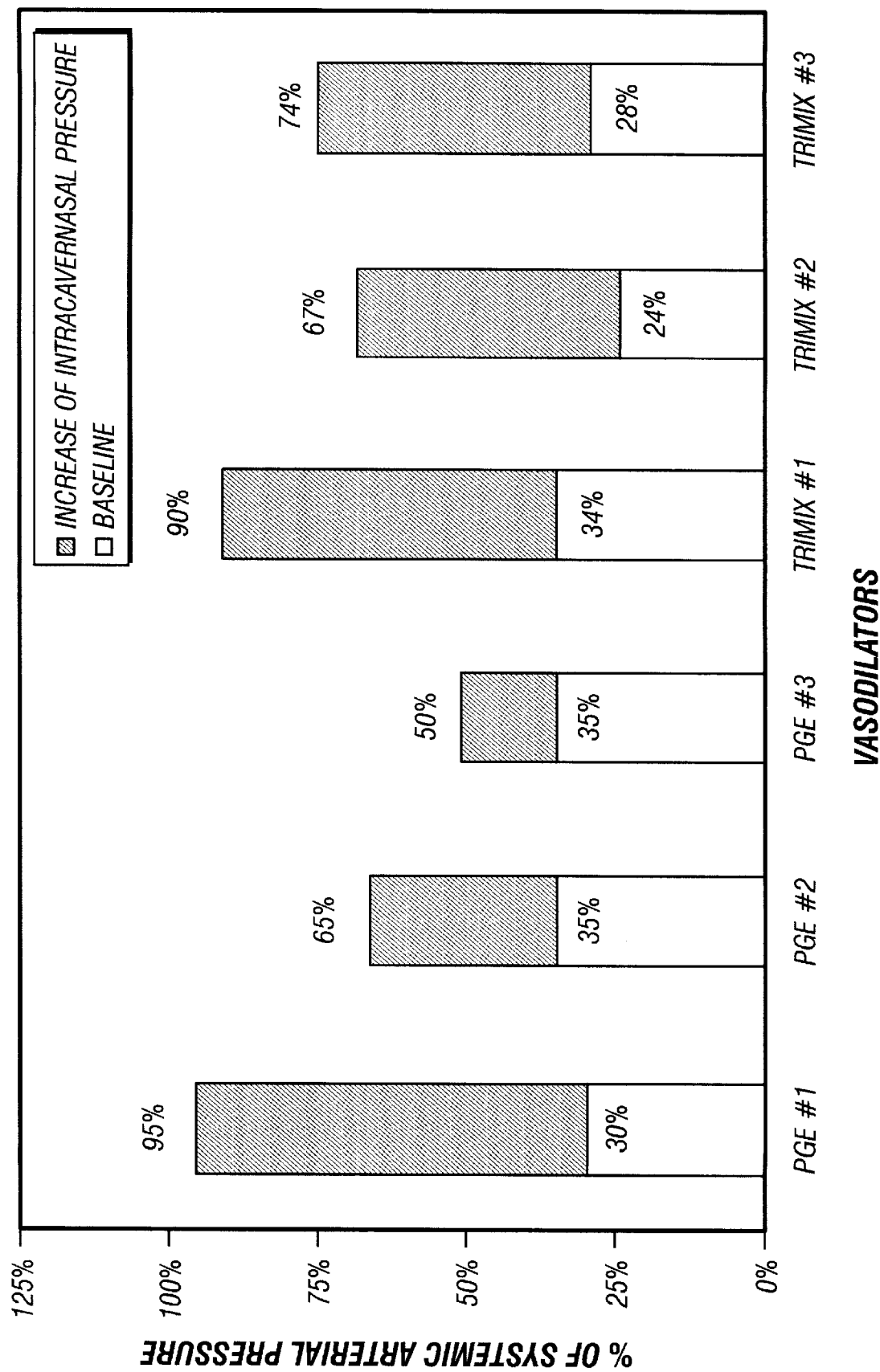
FIG. 7 shows a summary of the data shown in FIGS. 5 and 6, as described in Example II. Vasodilators applied are as indicated on the X-axis and the numbers for each bar indicate penile intracavernosal pressure as a Percent (%) of Systemic Aterial Pressure before (bottom) and after (top) electropulsing.

Animals were anesthetized with intramuscular injection of ketamine (35 mg/KG) and xylazine (5 mg/kg) and maintained with 0.2 ml intravenous bolus injections of pentobarbital (25 mg/ml) as needed. A 25 gauge angiocatheter was placed into the ear vein for continuous administration of physiologic saline solution. A 20 gauge angiocatheter was placed into the carotid artery and connected to a transducer for online measurement of systemic arterial pressure. A 23 gauge minicatheter was placed intracavernosally and connected to a transducer for measurement of penile intracavernosal pressure. A meander electrode (1 mm electrode width and 0.2 mm gap between two electrodes) was modified in open condom shape and placed around penile shaft and glans and connected to a BTX ECM600 pulse generator. Systemic arterial pressure and intracavernosal pressure (ICP) were continuously recorded before during and after topical application of PGE1 or trimix and electropulsing using an Astromed chart recorder. Intracavernosal pressure changes were normalized for arterial pressure and are presented as the percentage (%) of mean arterial pressure (FIG. 7). Erectile potency of each animal was confirmed by intracavernosal trimix injection at the end of the study.

One set of 6 electrical pulses without topical application of vasodilators on penile shaft and glans did not affect ICP. Six pulses with topical PGE1 alone also did not affect ICP.

PGE1 or trimix (100 µl) was applied on the penile shaft, glans and on the electrode followed by pulsed electrical field stimulation. Three sets of six pulses at 13 OHM, 400 µF, 50–60 V and 3 ms were applied and their effects on systemic and intracavernosal pressure were continuously recorded. The meantime of each set of six pulses was 1 minute. Stimulation with three sets of six pulses was repeated three times. If the animal failed to show erectile activity, additional PGE1 or trimix was applied on the glans and shaft and on the electrode and electric stimulation was repeated. This was continued until erectile activity was observed.

Effect of Topical PGE1 and Pulse Electrical Field Stimulation on Penile Erection Of the three animals studied, one animal achieved full penile erection, one animal developed partial erection and one animal showed only minor erectile activity. The following specific changes in intracavernosal pressure and systemic arterial pressure were noted during the studies:

PGE1 #1. Baseline systolic and diastolic arterial pressure was 111 and 84 mm Hg respectively. Baseline intracavernosal pressure was 30% of arterial pressure (PGE #1, FIG. 7). After application of PGE1 and 6 pulses at 13 OHM, 400 µF and 60V, intracavernosal pressure was 26% of arterial pressure. After the second and third sets of 6 pulses intracavernosal pressure decreased to 24% and 22% of arterial pressure respectively. Additional PGE1 was applied and stimulation was repeated. Intracavernosal pressure after the first, second and third set of 6 pulses was 22%, 19% and 16% of arterial pressure respectively. Additional PGE1 was applied. Since stimulation at 13 OHM, 400 µF and 60 V caused decrease of ICP, the remaining stimulations were performed at 13 OHM, 400 µF and 50 V. Electric stimulation with these parameters produced better erectile activity causing a gradual increase in intracavernosal pressure. Intracavernosal pressure after the first, second and third set of 6 pulses was 27%, 24% and 24% of arterial pressure respectively. Additional PGE1 was applied and pulsing was repeated at 13 OHM, 400 µF and 50 V. The first set of 6 pulses caused an increase in intracavernosal pressure to 58% of arterial pressure. The second set of 6 pulses caused further increase in intracavernosal pressure to 95% of systemic arterial pressure (PGE #1, FIG. 7). This animal developed full prolonged penile erection (FIG. 5A) and therefore did not require intracavernosal trimix injection to confirm erectile potency. At this time, the systolic and diastolic pressures were 120 mm Hg and 87 mm Hg respectively.

Figure 5A:
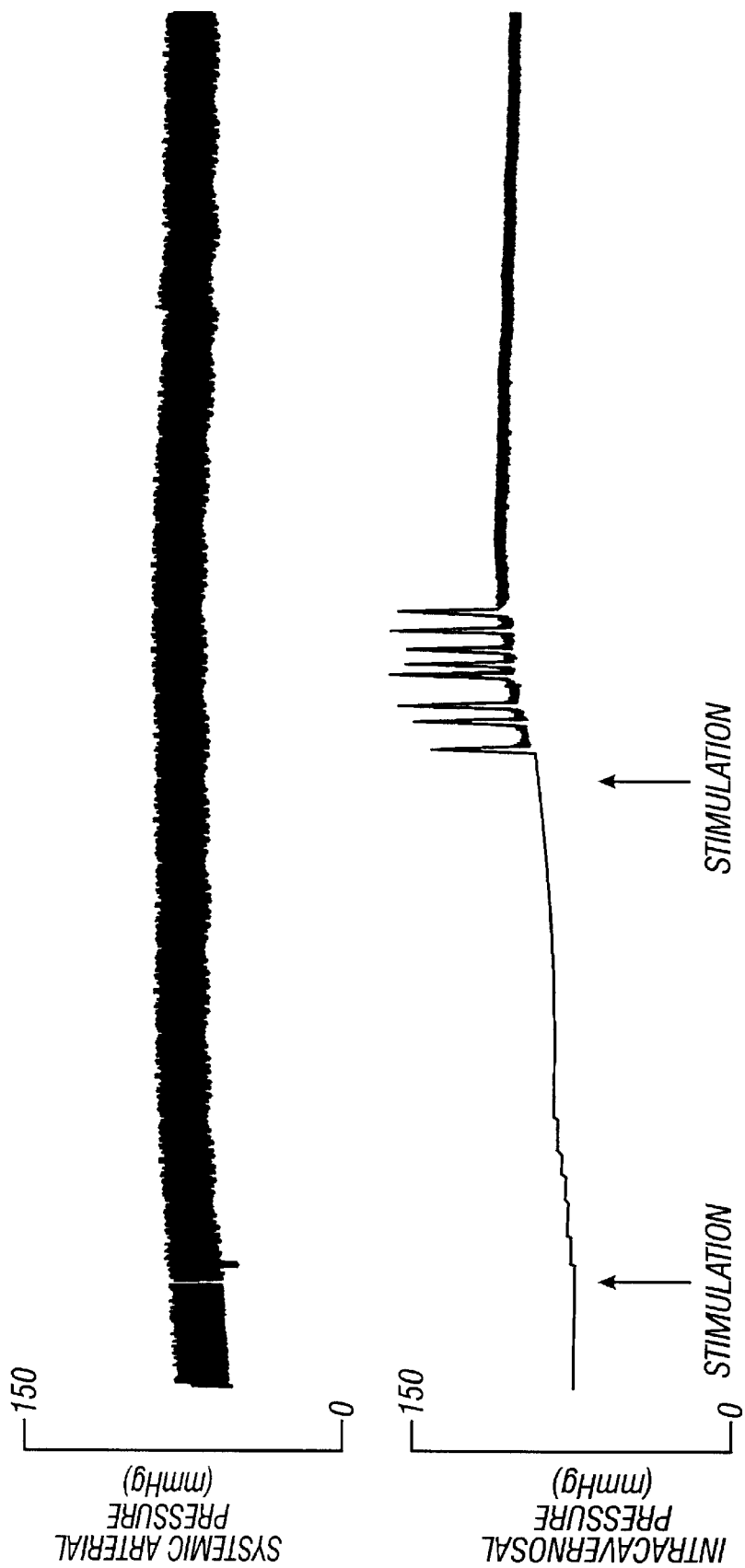
FIGS. 5A to 5C show the arterial (upper horizontal line) and penile intracavernosal pressure (lower horizontal line) in three rabbits in which PGE1 was applied to the penile shaft and glans followed by electropulsing as described in Example II. One animal achieved full penile erection (A), one animal developed partial erection (B), and one animal showed only minor erectile activity (C). Arrows indicate the point at which electrical stimulation occurred.
Figure 5B:
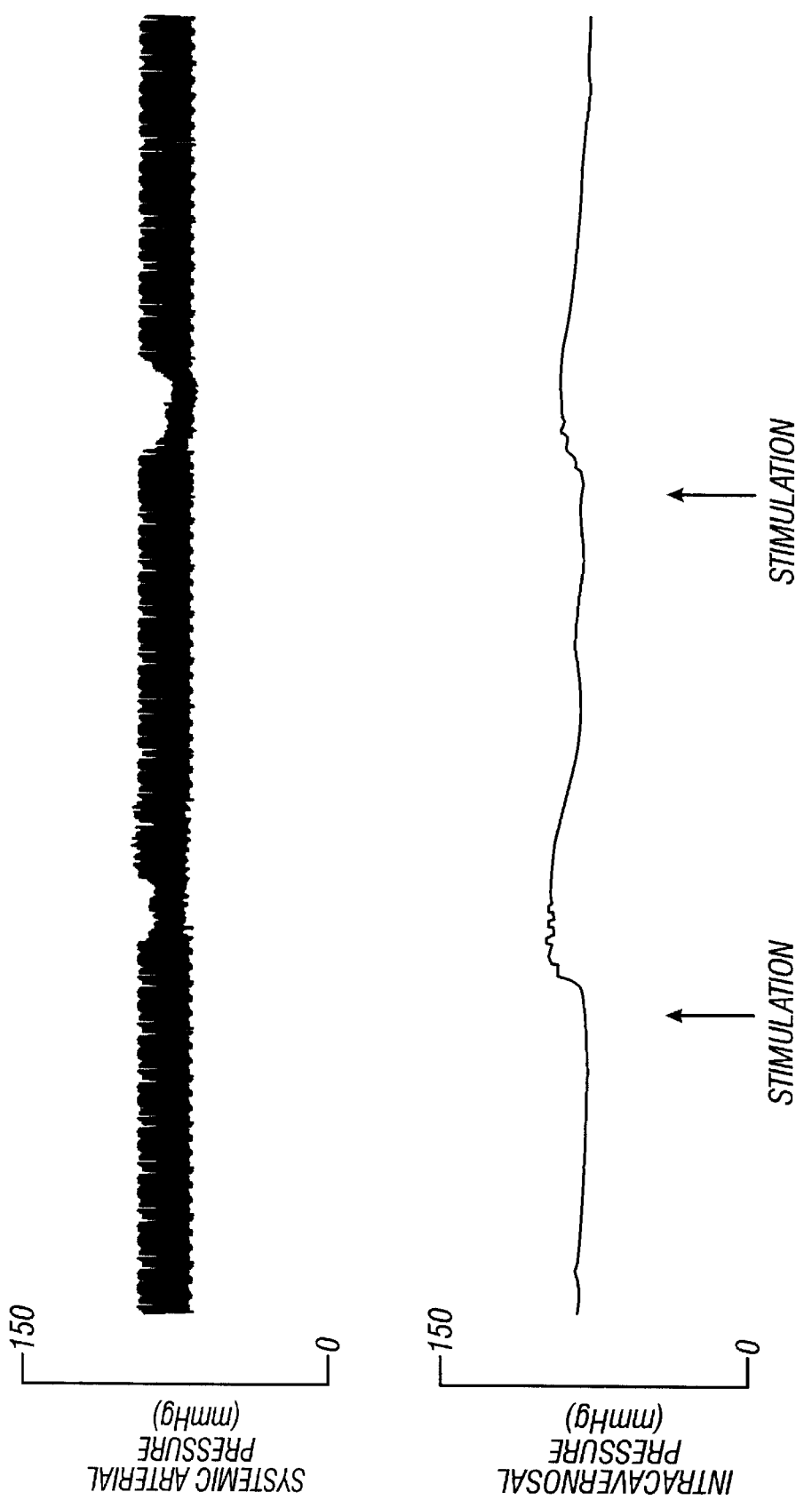

PGE1 #2. Baseline systolic and diastolic arterial pressures were 90 and 60 mm Hg respectively. Baseline intracavernosal pressure was 35% of arterial pressure (PGE #2, FIG. 7). After application of PGE1 and 6 pulses at 13 OHM, 400 µF and 50 V, the intracavernosal pressure was 47% of arterial pressure. After the second and third set of 6 pulses, intracavernosal pressure was 43% and 44% of arterial pressure respectively. Additional PGE1 was applied and pulsing was repeated. Intracavernosal pressure after the first, second and third set of 6 pulses was 36%, 42% and 40% of arterial pressure respectively. Another three sets of 6 pulses was applied. Intracavernosal pressure after the first, second and third set of 6 pulses was 48%, 44% and 41% of arterial pressure respectively. Another set of pulses was applied. Intracavernosal pressure after first, second and third set of 6 pulses was 45%, 45% and 44% of arterial pressure respectively. Additional PGE1 was applied and stimulation was repeated. Intracavernosal pressure after first, second and third set of 6 pulses was 43%, 47% and 47% of arterial pressure respectively. Additional PGE1 was applied and pulsing repeated. Intracavernosal pressure was first, second and third set of 6 pulses gradually increased to 57%, 58% and 60% of men arterial pressure respectively. Two additional sets of 6 pulses were applied. After the first set of pulses, intracavernosal pressure increased to 63% of arterial pressure. After the second set of stimulation, intracavernosal pressure increased to 65% of mean arterial pressure (PGE #2, FIG. 7). At this time, the animal was hypotensive (systolic and diastolic arterial pressure were 72 and 57 mm Hg respectively). This animal developed a partial penile erection (FIG. 5B). Intracavernosal trimix injection caused full penile erection.

Figure 5C:
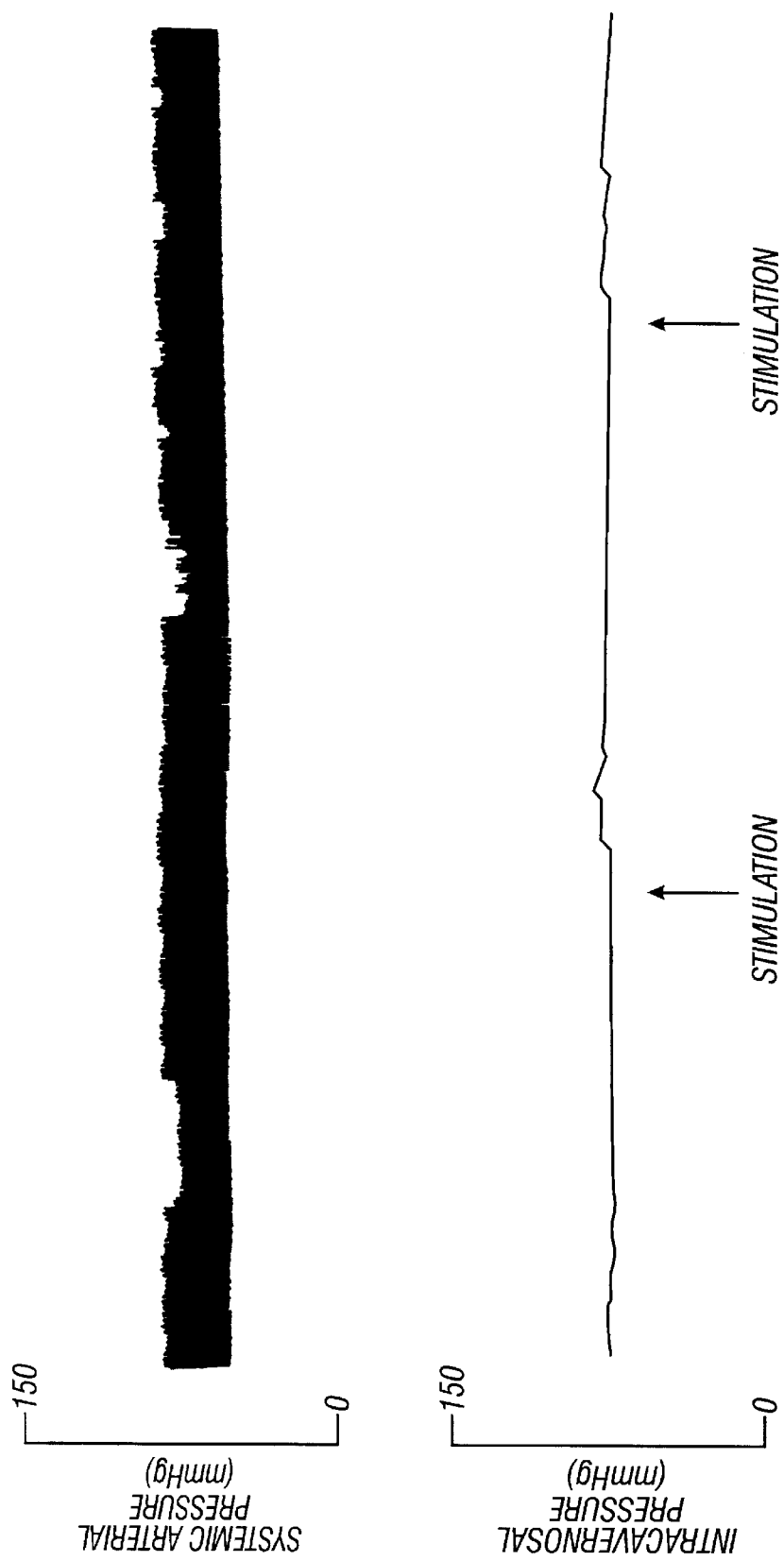

PGE1 #3. Baseline systolic and diastolic arterial pressures were 102 and 66 mm Hg respectively. Baseline intracavernosal pressure was 35% of arterial pressure (PGE #3, FIG. 7). After application of PGE1 and 6 pulses at 13 OHM, 400 µF and 50 V, intracavernosal pressure was 39% of arterial pressure. After the second and third set of 6 pulses, intracavernosal pressure was 35% and 30% of arterial pressure respectively. Additional PGE1 was applied and pulsing was repeated. Intracavernosal pressure after the first, second and third set of 6 pulses was 35%, 36% and 39% of arterial pressure respectively. Additional PGE1 was applied and three sets of 6 pulses were repeated. Intracavernosal pressure after the first, second and third set of 6 pulses was 45%, 45% and 47% of arterial pressure respectively. Another set of pulses was applied. Intracavernosal pressure after the first, second and third set of 6 pulses was 47%, 48% and 48% of arterial pressure respectively. Additional PGE1 was applied and pulsing repeated. Intracavernosal pressure after the first, second and third set of 6 pulses was 43%, 41% and 41% of mean arterial pressure respectively. Since a large amount of PGE1 was already applied on the glans and shaft, additional PGE1 was avoided while stimulation was continued. Twelve additional sets of 6 pulses were applied. In the final stimulation, intracavernosal pressure after the first, second and third pulses was 46%, 50% and 50% of arterial pressure respectively (PGE #3, FIG. 7). At this time, the systolic and diastolic pressure was 98 mm Hg and 63 mm Hg respectively. This animal showed some erectile activity but the quality of erection was poor (FIG. 5C). Intracavernosal trimix injection caused full penile erection.

Figure 6A:
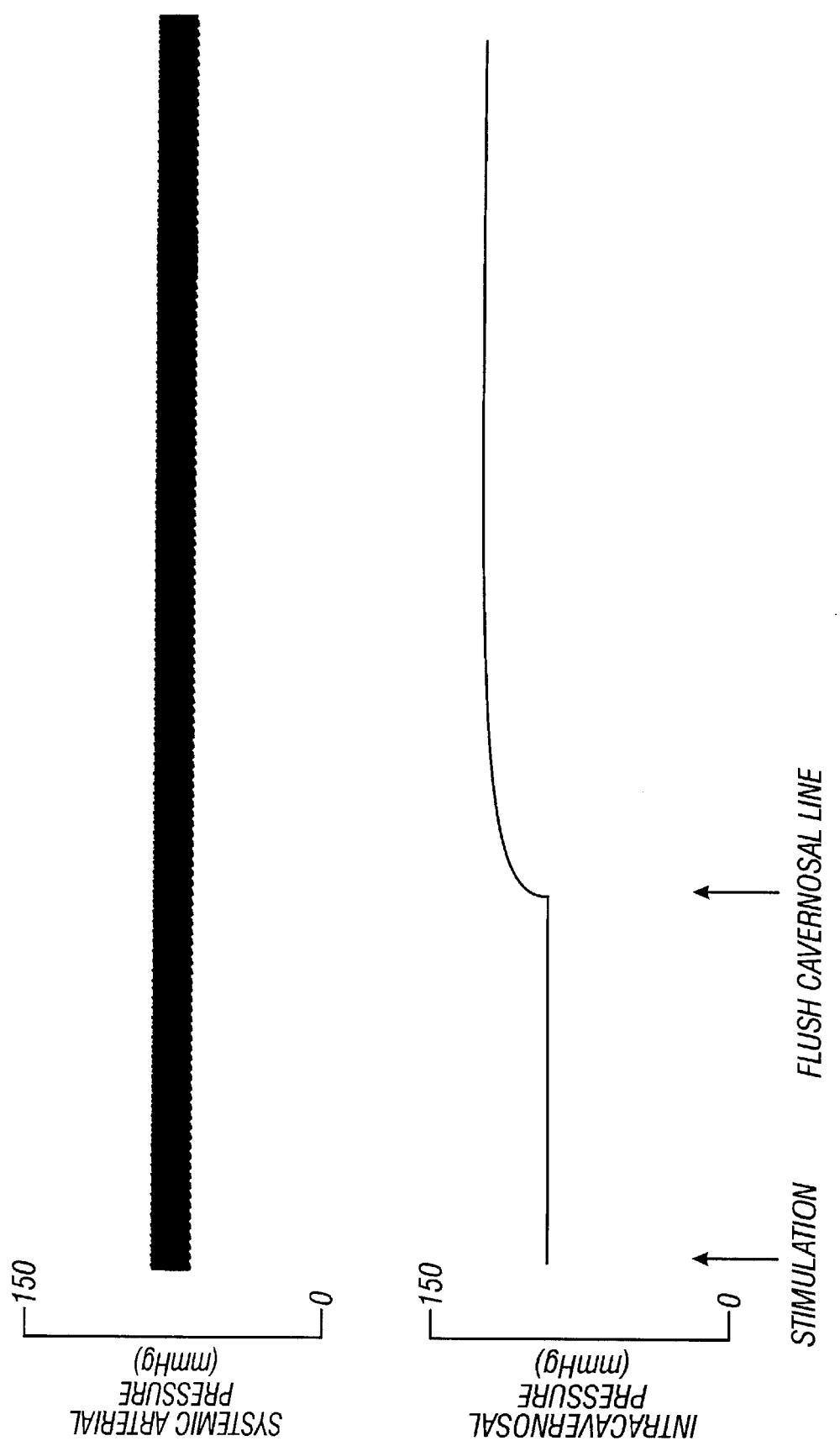
FIGS. 6A to 6C show the arterial and penile intracavernosal pressure in three rabbits in which trimix (papavarine, phentolamine and PGE1) was applied to the penile shaft and glans followed by electropulsing as described in Example II. One animal achieved full penile erection (A), while the other two animals developed partial erection (B) and (C). Arrows are as indicated.

Effects of Topical Trimix and Pulse Electrical Field Stimulation on Penile Erection Of the three animals studied, one animal achieved full penile erection while the other two animals showed partial erection. The following specific changes in intracavernosal pressure and systemic arterial pressure were noted during the experiments:

Trimix #1. Baseline systolic and diastolic arterial pressure was 105 and 84 mm Hg respectively. Baseline intracavernosal pressure was 34% of arterial pressure (Trimix #1, FIG. 7). After one set of 6 pulses alone (without trimix) at 13 OHM, 400 µF and 50 V, intracavernosal pressure was 33% of arterial pressure. After the second and third set of 6 pulses, intracavernosal pressure was 36% and 36% of arterial pressure respectively. After application of trimix, intracavernosal pressure after the first, second and third set of 6 pulses was 35%, 36% and 38% of arterial pressure respectively. Additional trimix was applied and pulsing was repeated. Intracavernosal pressure after the first, second and third set of 6 pulses was 40%, 40% and 42% of arterial pressure respectively. Additional trimix was applied and pulsing was repeated. After the first, second and third set of 6 pulses, intracavernosal pressure was 52%, 55% and 67% of arterial pressure respectively. Another three set of 6 pulses was applied. Intracavernosal pressure after the first, second and third pulses was 70%, 74% and 90% of arterial pressure respectively (Trimix #1, FIG. 7). At this time, systolic and diastolic pressures were 107 mm Hg and 82 mm Hg respectively. This animal developed a full prolonged penile erection (FIG. 6A).

Figure 6B:
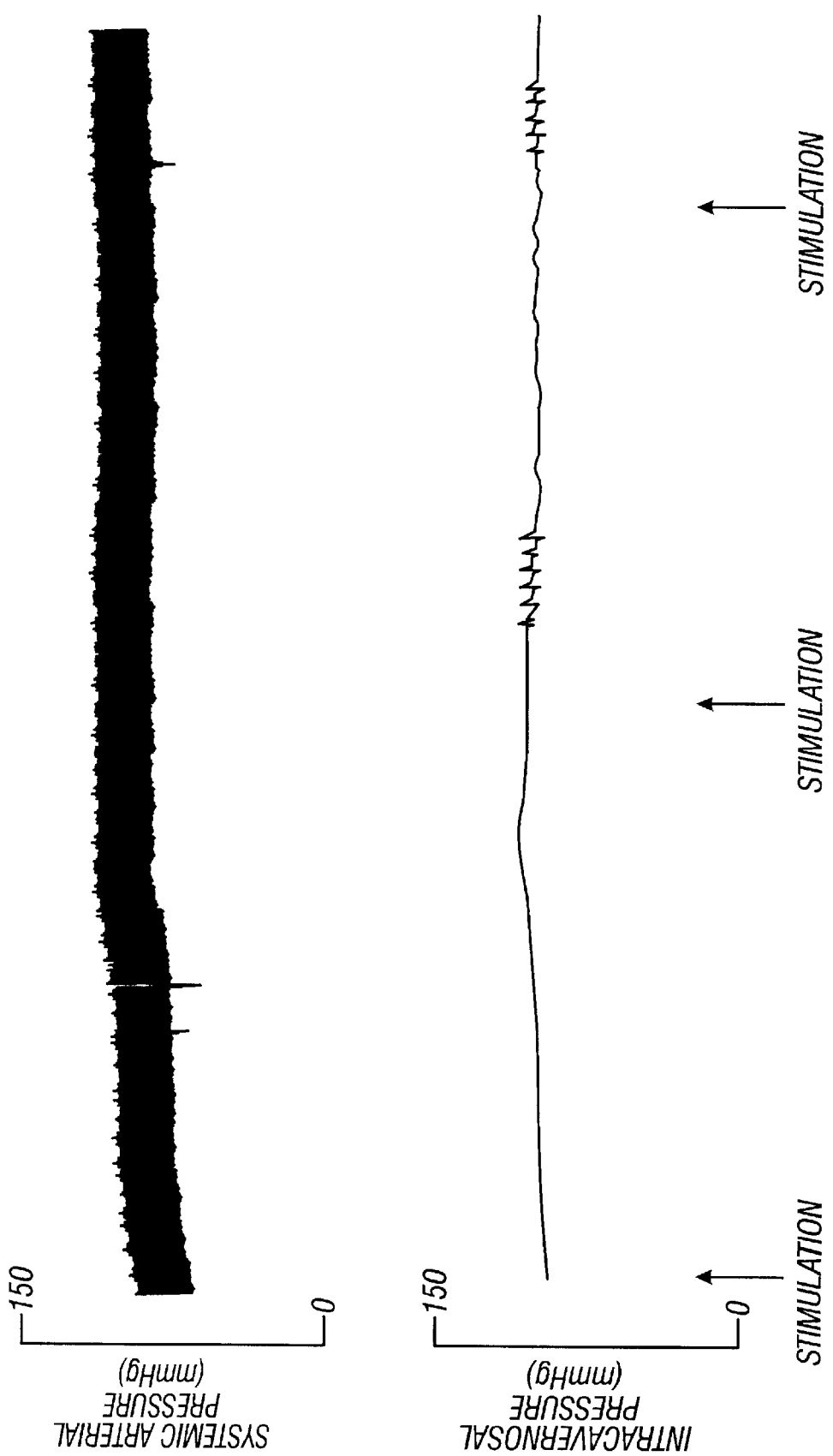

Trimix #2. Baseline systolic and diastolic arterial pressure was 96 and 78 mm Hg respectively. Baseline intracavernosal pressure was 24% of arterial pressure (Trimix #2, FIG. 7). One set of 6 pulses alone (without trimix) at 13 OHM, 400 µF and 50 V did not affect intracavernosal pressure. After application of trimix and 6 pulses at 13 OHM, 400 µF and 50 V, intracavernosal pressure was 37% of arterial pressure. After the second and third set of 6 pulses, intracavernosal pressure was 41% and 40% of arterial pressure respectively. Another three sets of 6 pulses was intracavernosal pressure 39%, 42% and 43% of arterial pressure respectively. Additional trimix was applied and pulsing was repeated. Intracavernosal pressure after the first, second and third set of 6 pulses was 47%, 52% and 49% of arterial pressure respectively. Another three sets of 6 pulses were applied. Intracavernosal pressure after the first, second and third set of 6 pulses was 49%, 55% and 55% of arterial pressure respectively. Another three sets of 6 pulses were applied. Intracavernosal pressure after the first, second and third set of 6 pulses was 55%, 55% and 64% of arterial pressure respectively. Additional three sets of 6 pulses were applied. Intracavernosal pressure after the first, second and third pulses was 53%, 53% and 59% of arterial pressure respectively. Additional trimix was applied and pulsing repeated. Intracavernosal pressure after the first, second and third set of 6 pulses was 63%, 65% and 69% of arterial pressure. Another three sets of 6 pulses were applied. Intracavernosal pressure after the first, second and third set of 6 pulses was 64%, 65% and 67% of arterial pressure respectively (Trimix #2, FIG. 7). At this time, systolic and diastolic arterial pressure were 90 and 57 mm Hg respectively. This animal developed a partial penile erection (FIG. 6B). Intracavernosal trimix injection caused full penile erection.

Figure 6C:
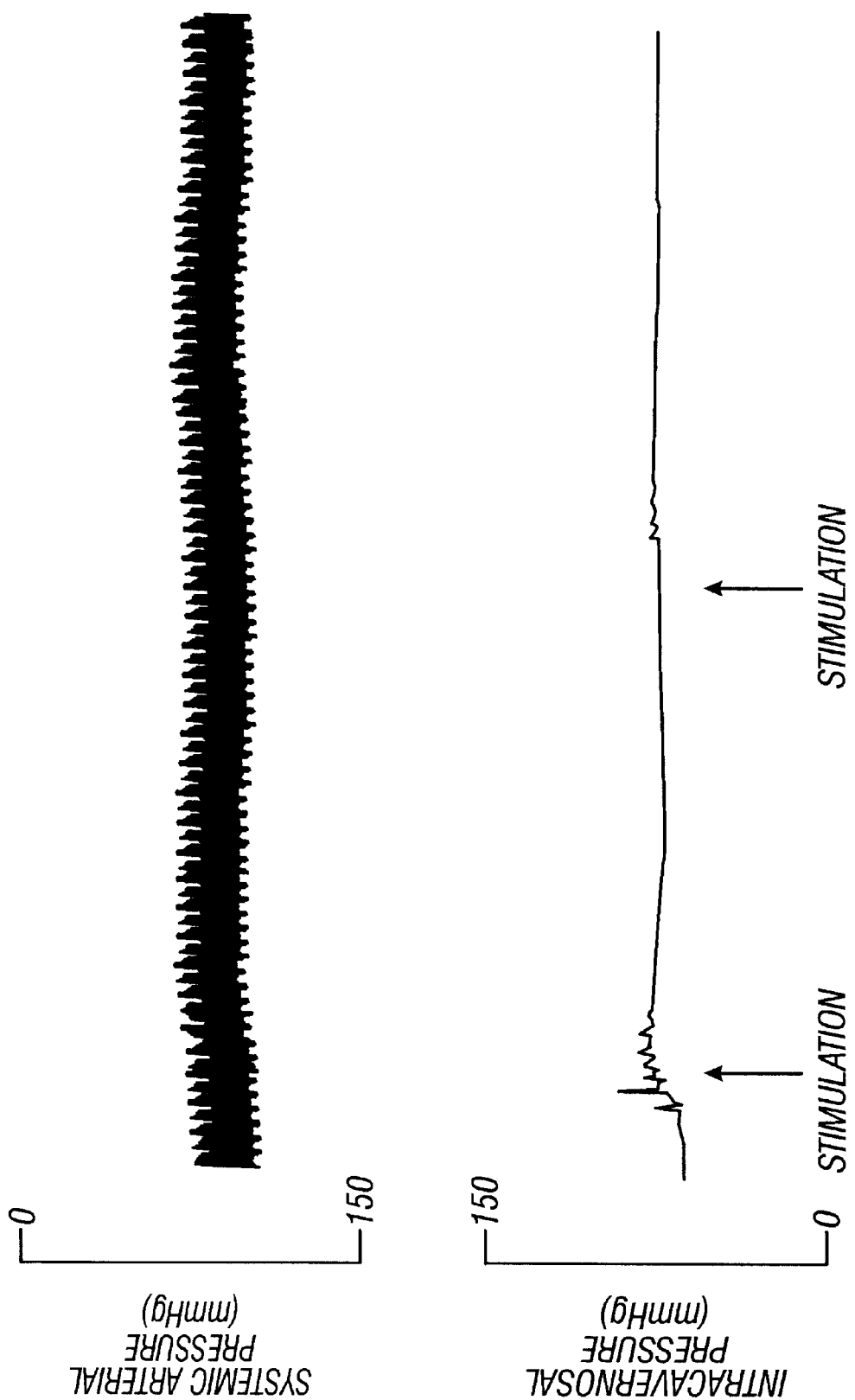

Trimix #3. Baseline systolic and diastolic arterial pressure was 93 and 69 mm Hg respectively. Baseline intracavernosal pressure was 28% of systemic arterial pressure (Trimix #3, FIG. 7). One set of 6 pulses at 13 OHM, 400 µF and 50 V did not affect intracavernosal pressure. After application of trimix and 6 pulses at 13 OHM, 400 µF and 50 V, intracavernosal pressure was 33% of arterial pressure. After the second and third set of 6 pulses, intracavernosal pressure was 34% and 33% of arterial pressure respectively. Another three sets of 6 pulses were applied. Intracavernosal pressure after the first, second and third set of 6 pulses was 45%, 43% and 43% of arterial pressure respectively. Another three sets of 6 pulses were applied. Intracavernosal pressure after the first, second and third set of 6 pulses was 43%, 43% and 43% of arterial pressure respectively. Additional trimix was applied and three sets of 6 pulses were repeated. Intracavernosal pressure after the first, second and third set of 6 pulses was 63%, 56% and 62% of arterial pressure respectively. Another three sets of 6 pulses were applied. Intracavernosal pressure after the first, second and third set of 6 pulses was 65%, 67% and 71% of arterial pressure respectively (Trimix #3, FIG. 7). Additional pulsing did not further increase intracavernosal pressure. At this time, the systolic and diastolic pressure was 93 mm Hg and 60 mm Hg respectively. This animal developed a partial short lived erection (FIG. 6C). Intracavernosal trimix injection caused full penile erection.

To summarize, in the three animals with topical PGE1 application, pulsed electric field stimulation caused full penile erection in the first animal, partial erection in the second animal and relatively poor but detectable erectile activity in the third animal. In the three animals with topical trimix application, pulsed electric field stimulation caused full penile erection in the first animal while causing partial erection in the second and third animals. Pulsed electrical stimulation with topical trimix appears to be slightly more effective in producing erectile activity compared to pulsed electrical stimulation with topical PGE1.

These studies show that topical application of vasodilators in conjunction with electric pulsing induces erectile activity in the rabbit. Although the effect of electric pulsing in producing erectile activity varied among the animals, at least some amount of erectile activity was produced up to a full prolonged erection in every animal.

EXAMPLE III

This example shows that topical application of PGE1 or trimix (papavarine, phentolamine and PGE1) on the penile glans or shaft without application of electric pulsing fails to induce penile erection in rabbits. This example also shows that applying electric pulsing alone (without application of vasodilator) fails to induce penile erection in rabbits.

New Zealand White rabbits (n=6) weighing between 3–3.5 kg were divided into three groups for studies of the effect of topical PGE1 crystals on erectile function (n=2); for studies of the effect of topical trimix on erectile function (n=2); and for studies of the effect of electric pulsing on penile erection. The concentration of PGE1 for each topical application was 10 mg/100 1 and the concentration oftrimix for each topical application comprised 10 mg papavarine+ 0.5 mg phentolamine+0.2 mg PGE1 in 100 $\mu$l.

Figure 8:
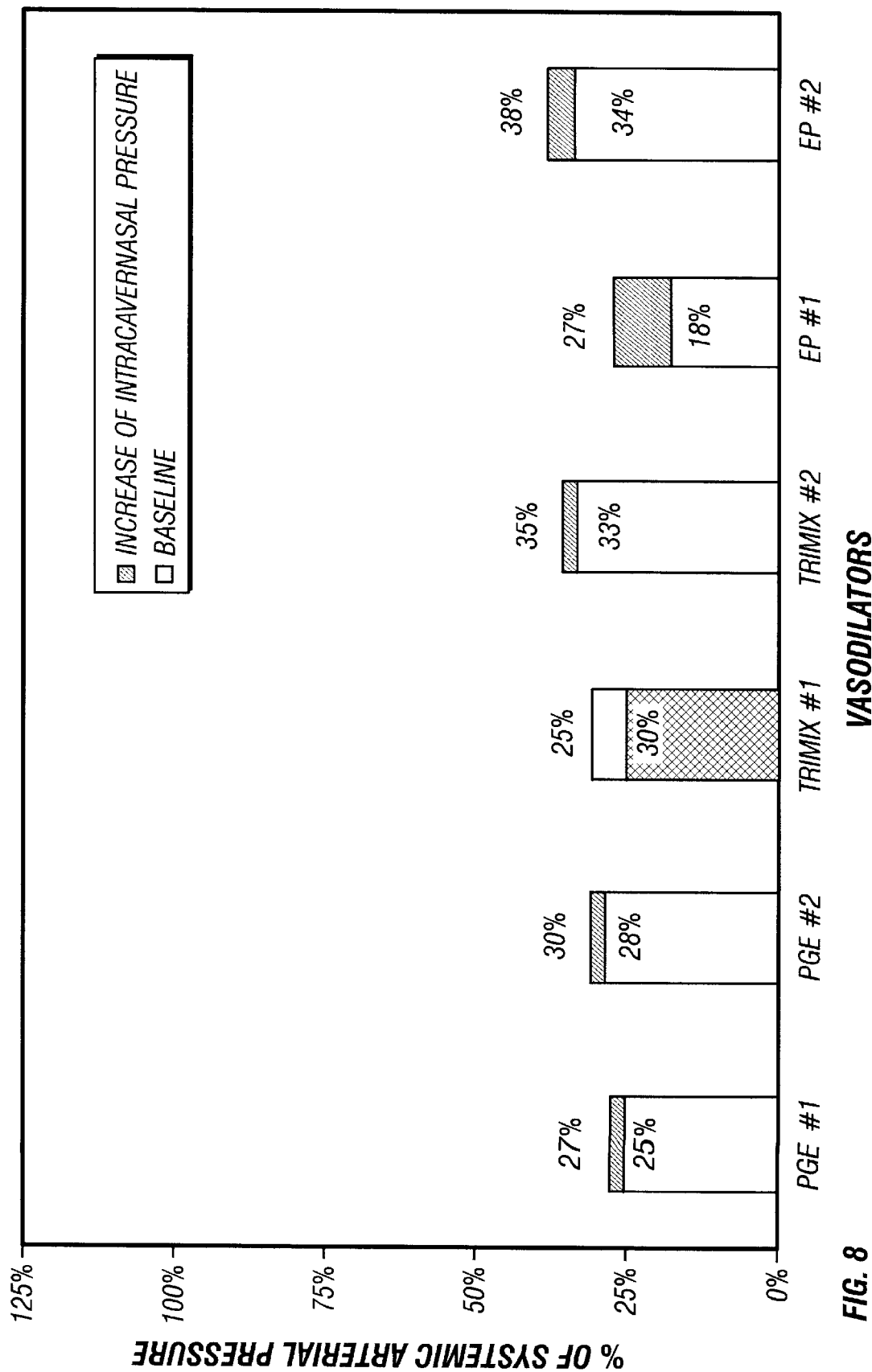
FIG. 8 shows a summary of the control studies described in Example III. Penile intracavernosal pressure for each (no electropulsing: PGE #1, PGE #2, Trimix #1, Trimix #2; and with electropulsing alone: EP#1 and EP#2) is indicated as the Percent (%) of Systemic Arterial Pressure (bar). The bottom number for each bar is the percent before PGE1 or trimix application or electropulsing alone; the top number for each bar is the percent after PGE1 application, trimix application or electropulsing, each alone.

Animals were anesthetized as before. A 25 gauge angiocatheter was placed into the ear vein for continuous administration of physiologic saline solution. A 20 gauge angiocatheter was placed into the carotid artery and connected to a transducer for on-line measurement of systemic arterial pressure. A 23 gauge minicatheter was placed intracavernosally and connected to a transducer for measurement of intracavernosal pressure. A meander electrode was placed around the penile shaft and glans and connected to a BTX ECM600 pulse electrical field generator. Arterial and intracavernosal pressures were continuously recorded on an Astromed chart recorder throughout the procedure. Intracavernosal pressure changes were normalized for arterial pressure and are presented as the percentage (%) of Systemic Arterial Pressure (FIG. 8). Erectile potency of rabbits was confirmed by intracavernosal trimix injection at the end of the studies.

Studies with Topical PGE1 and with Topical Trimix without Electric Pulse Stimulation Baseline systemic arterial pressure and intracavernosal pressure were recorded. PGE1 (10 mg/100 $\mu$l) or trimix (10 mg papavarine+0.5 mg phentolamine+0.2 mg PGE1 in 100 $\mu$l) was applied to the glans, penile shaft and electrode. After three minutes, a second dose of PGE1 or trimix was applied. Topical application of PGE1 or trimix on penile glans, shaft and electrode was repeated up to four doses in three minute intervals. After topical application, systemic arterial and intracavernosal pressures were recorded for an additional ten minutes.

In two animals, topical administration of four doses of PGE1 on the glans, penile shaft and electrode without pulsed electrical field stimulation did not affect systemic and intracavernosal pressures (PGE1 #1 and #2, FIG. 8). Baseline intracavernosal pressures before administration of PGE1 in the two animals were 25% and 28% of systemic arterial pressure. After the fourth dose application of PGE1, systemic and intracavernosal pressures in the two animals were 27% and 30% of systemic arterial pressure. These differences after topical PGE1 were not statistically significant compared to those recorded before PGE1 administration. Intracavernosal pressures after intracavernosal trimix injection of the two animals, however, reached 92% and 95% of systemic arterial pressure, confirming erectile potency.

In two animals, topical administration of four doses of trimix on the glans, penile shaft and electrode without pulsed electrical field stimulation did not affect systemic and intracavernosal pressures (Trimix #1 and #2, FIG. 8). Baseline intracavernosal pressures before administration of trimix in the two animals were 30% and 33% of systemic arterial pressure. After the fourth dose of topical trimix, intracavernosal pressures in the two animals were 25% and 35% of systemic arterial pressure. These differences after topical trimix were not statistically significant compared to those recorded before trimix administration. Intracavernosal pressures after intracavernosal trimix injection of in the two animals, however, reached 90% and 97% of systemic arterial pressure, confirming erectile potency.

Studies with Electric Pulse Stimulation without Topical Vasodilators

Baseline systemic arterial pressure and intracavernosal pressure were recorded. After application of 100 $\mu$l buffer on glans, penile shaft and electrode, one set of six pulses (50 V, 13 OHM and 400 $\mu$F) was applied. After this the second and third set 6 pulses were applied in one minute intervals. After three sets of six pulses were applied, additional buffer (100 $\mu$l) was applied on the glans, penile shaft and electrode. The three sets of six pulses were repeated while adding buffer after every three sets of six pulses. This was repeated until a total of 20 sets of electric pulsing. After the 20th set of electric pulsing, systemic arterial and intracavernosal pressures were measured for an additional 10 minutes.

Without topical administration of vasodilators, 20 sets of six electric pulses applied to the glans and penile shaft of two animals did not affect systemic and intracavernosal pressures (EP#1 and #2, FIG. 8). Baseline intracavernosal pressures before electric pulsing in the two animals were 18% and 34% of systemic arterial pressure. After the 20th set of electric pulsing intracavernosal pressures were statistically similar to those recorded before electrical field stimulation. After the 20th set of electric pulsing intracavernosal pressures in the two animals were 27% and 38% of systemic arterial pressure. These differences after electric pulsing were not statistically significant compared to those recorded before stimulation. Intracavernosal pressures after intracavernosal administration of trimix in the two animals, however, reached to 91% and 95% of systemic arterial pressure confirming erectile potency.

These studies show that transdermal introduction of a topical application of vasodilators (e.g., PGE1 and trimix) require applying an electric pulse for inducing erectile activity. These studies also show that an electric pulse without topical PGE1 or trimix is not capable of producing erectile activity in the rabbit.

EXAMPLE IV

This example shows that PGE1, used for self-injection therapy in erectile dysfunction, can be transdermally introduced into human skin in vitro and human penile skin by electric pulsing alone, or in combination with iontophoresis, thereby providing a non invasive mode of drug delivery.

Materials

Prostaglandin E1 (PGE1) and tritium-labeled Prostaglandin E1 ($^3$H-PGE1) was obtained from Sigma (St. Louis, Mo.). Labeled drug was received in 7:3 ethanol:water mixture. The drug was protected from light during all studies, which were done in triplicate. Scintillation cocktail (ULTIMA-GOLD™) and SOLVABLE™ tissue and gel solubilizer were obtained from Packard (Meriden, CT). Human cadaver skin and penile skin obtained from skin banks had been frozen within 12 hours of death and supplied as full thickness skin, unless otherwise specified. Once received, the skin was stored at −80° C. and then thawed just before use. Full thickness or dermatomed human cadaver skin or penile skin was used. Buffer components and other chemicals were obtained from Fisher Scientific (Pittsburgh, Pa.); silver-silver chloride electrodes were purchased from In Vivo Metric (Healdsburg, Calif.); and meander electrodes were from Genetronics, Inc. (San Diego, Calif.).

Solution Studies

For these studies, the drug was in solution though the final formulation may have been a suspension due to the addition of latex or dextran particles. PGE1 (5.6 μg) was dissolved in ethanol:water (7:3) and spiked with $^3$H-PGE1. A few microliters of this solution was placed on full thickness human skin and covered with a meander electrode, which consists of an interweaving array of metal fingers coated on a thin plastic film. Pulses were applied via these metal fingers on the meander electrode creating an electric field that breaks down the stratum corneum of the skin. Slight pressure was applied on the electrode during pulsing either by clamping the whole set-up on a table top or by clamping the set-up on the upper half of a Franz cell. Further details on this pressure-mediated "electroincorporation" technique can be found in Hofmann et al., Bioelectrochem. Bioenerg. 38 (1995) 209–222 and Zhang et al., Bioelectrochem. Bioenerg. 42 (1997) 283–292. Following table top pulsing, the skin was transferred in some cases to glass diffusion cells. In this case, the donor and receptor solutions were filled with 4 ml of HEPES buffer and iontophoresis was applied in some cases using silver/silver chloride electrodes.

Suspension Studies

For these studies, the drug was in suspension. In a typical suspension study, prostaglandin (PGE1 and $^3$H-PGE1) was dissolved in ethanol and then ethanol was removed by drying under nitrogen. This procedure helped to molecularly disperse PGE1 and $^3$H-PGE1 together. The dried powder was then resuspended in 10 mM phosphate buffer so that a suitable concentration of prostaglandin in a small volume (typically, few μl) is achieved. The analysis was then done by liquid scintillation counting. In cases where immunoassay was used, $^3$H-PGE1 was not used but PGE1 was still recrystallized from ethanol so that a similar particle size distribution is obtained. Particles of the recrystallized suspension were mostly needle shaped, with a width of about 1 micron and a length of about 5 microns. Some spherical particles of 1–2 micron size were also seen. The original particle size of PGE1 received from supplier was in the range of 5–20 microns, seen as crystalline particles, though some particles as large as 45 micron were also seen. Recrystallization seems to have resulted in a more uniform particle size distribution. When the Franz cell set-up was used, the skin was cut into 1 inch square pieces (pulsing area 0.64 cm$^2$) for electroporation experiments, and appropriate controls were treated with PGE1 but not pulsed. The skin was placed on Franz cell, the drug suspension was added, meander electrode with a well created by a double-sided tape was placed on this solution, a parafilm was placed on meander electrode and then a metal disc was placed on the top before clamping the donor chamber for intimate contact. More consistent results were obtained when the suspension was contained in this well created on the meander electrode using double sided tape an the whole experiment was done on the Franz cell setup. In the absence of this well, the solution under meander electrode could be squeezed out by the applied pressure.

The experimental group pieces of skin were typically pulsed with 6 pulses of 100 V or 120V and 10–20 ms duration. In some cases, 6 additional pulses were applied after a one minute rest. The skin was then left on the set-up for 15 minutes, at which time a receiver sample was taken and the skin was removed. In some studies, additional sampling was done to study the slow release of drug from the skin. Following the study, the skin was cleaned with three cotton swabs wetted with buffer (with dry tips in between) to wipe out the treated side, cut into several pieces, sometimes followed by one tape stripping. The blade used for cutting and the petridish in which the skin was cut were washed with the skin solubilizer and the skin and washings were transferred to solubilizer and digested at 75° C. for 2 days. For experiments using ELISA assay, the skin was not dissolved in solubilizer but rather extracted by the procedure described hereinbelow.

Skin Extraction & Immunoassay

Skin samples were weighed and then cut into small pieces. The skin was then placed into a beaker with 10 ml PBS buffer, homogenized using a homogenizer (OMNI 5100) at moderate speed and it was passed through samples for about 4–5 minutes. The homogenate was acidified with 1 N HCl to a pH of 3.5 to 4.0, and transferred to a siliconized glass tube; 2 ml of phosphate buffer was used to transfer the residue from the beaker. The skin homogenate was then extracted with 20 ml of ethyl acetate and 4500 dpm of $^3$H-PGD2 was added for measurement of extraction efficiency.

Sample was vortexed for 10 mins and centrifuge at 3000×g for 15 mins. The top layer was drawn off into a siliconized tube and extracted with another 20 ml ethyl acetate, followed by vortexing and centrifugation, as before. The ethyl acetate fractions were pooled, dried under nitrogen and resuspended in 3 ml of ethyl acetate; aliquots were removed for determination of extraction efficiency and prostaglandin analysis. PGE1 content was determined using an enzyme immunoassay (EIA) kit (Assay Design Inc., MI). Samples were aliquoted as follows: 500 μl (suspended in EIA buffer) for EIA, 1000 μl (suspended in 10 mM Phosphate buffer) for measurement of recovery; the rest of the 1.5 ml sample was stored in ethyl acetate at −20° C. The EIA aliquot was dried and suspended in 500 μl of assay buffer provided with the kit and the assay was performed according to kit instructions. The optical density of the samples was read using a BioRad microplate reader model 4500 and sample concentrations were calculated using microplate reader software version 2.03 by BioRad and Microsoft Excel, using dilution and extraction efficiency into consideration.

Solution Formulation

Figure 9:
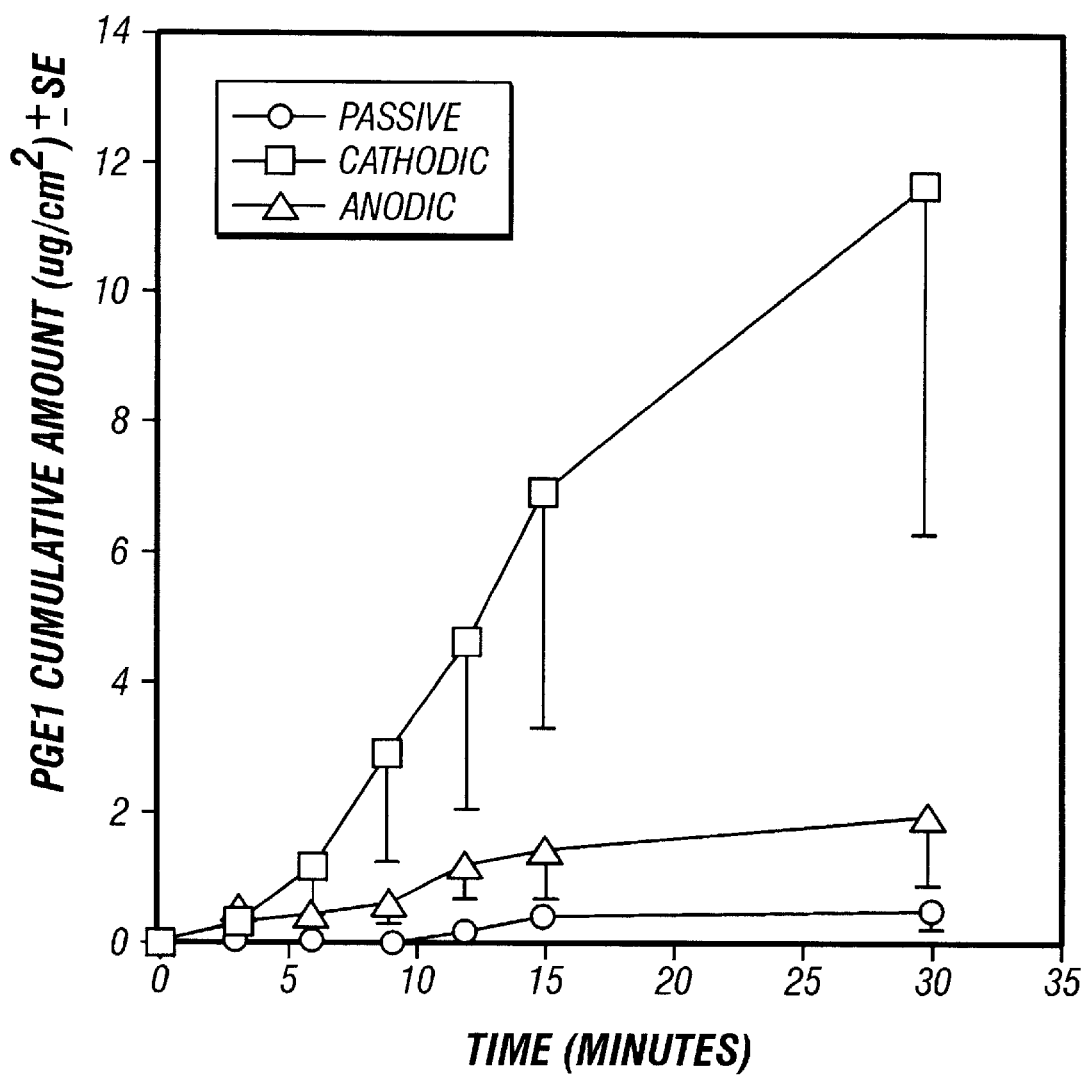
FIG. 9 shows the delivery of PGE1 solution across dermatomed human skin to receptor in glass diffusion cells combined with 30 min of iontophoresis (PGE1 cumulative amount, µg/cm² skin) with anode in donor (anodic) or cathodes in donor (cathodic) and a control without iontophoresis (passive) over time (X-axis). Error bars extend from each point.

A solution study with iontophoresis in a diffusion cell was first carried out to establish the electrode polarity for optimal delivery. It was observed that 30 minutes of iontophoresis could increase the permeation of PGE1 across skin several fold over passive diffusion, with the highest delivery under cathode (FIG. 9). The corresponding amount in the skin at the end of the study was 1.21±0.76 μg/cm$^2$ (passive), 0.69±0.14 μg/cm$^2$ (cathode), and 0.77±0.1 μg/cm$^2$ (anode). The use of pulsing (6 pulses of 100 V, 10 ms each) prior to iontophoresis increased the amount delivered into skin. This was true irrespective of whether pulses were applied by meander or wire (cathode) electrode. The amount with meander electrodes was 2.42±1.09 μg/cm$^2$ in skin and 2.77±1.0 μg/cm$^2$ in receptor, while with wire electrodes, the amount in skin was 4.23±2.09 μg/cm$^2$ and in receptor was 1.02±0.08 μg/cm$^2$.

Pulsing Solution Formation with Particles

Figure 10:
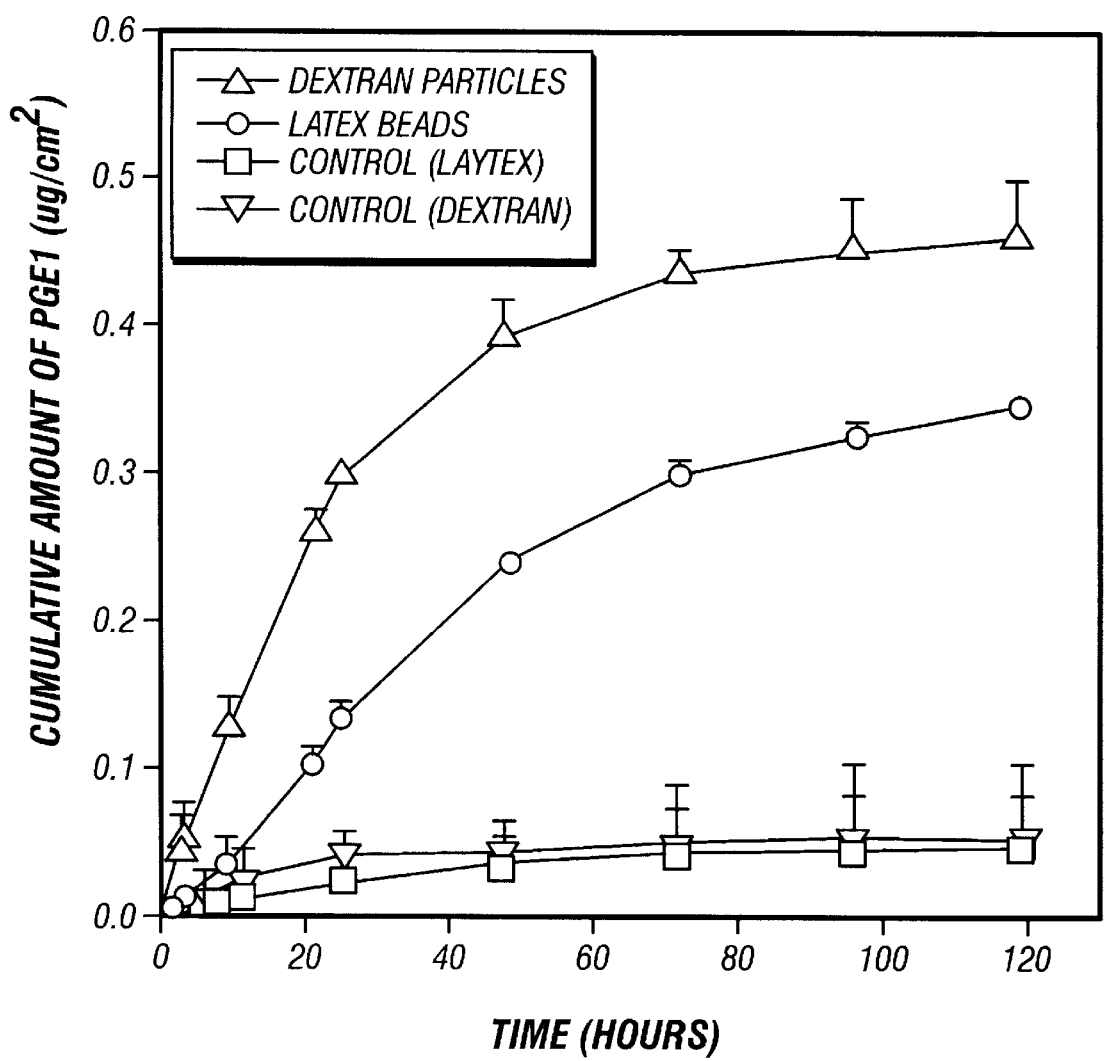
FIG. 10 shows the delivery of PGE1 solution with latex or dextran particles into full thickness human skin by pulsing and subsequent slow release into receptor solution after mounting on transdermal diffusion cells. Error bars extend from each point.

PGE1 (5.6 μg) was dissolved in 7:3 ethanol:water (20 μl) and either latex (2.5%) or dextran (5%) particles were added. The formulation was placed on full-thickness human cadaver skin, and three pulses (120V, 10 ms each) were applied by meander electrodes. Following electroporation, the skin was mounted on transdermal glass diffusion cells. The exposed area of the skin to the receiver compartment was the same 0.64 cm$^2$ to which the drug solution was applied. The receptor compartment contained 4 ml of HEPES buffer. The amount of prostaglandin coming out from skin into the receptor compartment was measured as a function of time (FIG. 10). Control experiments were also done in which all variables were same but no pulse was applied. Following the study, the skin was removed, incubated with a tissue solubilizer and then analyzed to quantitate the amount of PGE1 remaining in the skin. Based on the cumulative permeation and the amount that remains in the skin at the end of the study, the amount of PGE1 in skin just after pulsing was $0.46\pm0.03$ $\mu g/cm^2$ for the latex particle study and $0.56\pm0.09$ $\mu g/cm^2$ or the dextran particle study. Thus, it appears that of the amount delivered into skin by pulsing, about 80% is released into receptor over a period of 5 days. This was followed by a higher concentration study, in which 200 $\mu g$ PGE1 was placed on the skin and pulsed with latex particles. The delivery was again higher in presence of pulsing.

The effect of increasing concentration of prostaglandin was investigated, applying 5, 20, 100 and 200 $\mu g$ of PGE1 to full thickness skin, in a 8 $\mu l$ volume. Six pulses (120V, 20 ms each) were applied with a 5-minute post pulse application of pressure. For the control group without dextran, everything was the same except pulses were not applied. Results indicate that a higher amount of PGE1 was delivered into the skin as the PGE1 concentration increased.

Electroporation of PGE1 Suspension

In a study with full thickness skin (average thickness 0.73 mm), a 300 $\mu g/6$ $\mu l$ PGE1 suspension was applied with a meander electrode by six pulses (100 V, 20 ms) followed by another six pulses after a one minute rest. The amount of PGE1 in pulsed skin was found to be $3.08\pm0.68$ $\mu g/cm^2$, while in control skin was $1.62\pm0.47$ $\mu g/cm^2$. No PGE1 was detected in receiver at the end of the study (15 minutes after pulsing), suggesting that the drug was not driven across the skin. The p-value on a two-tail test is 0.023. Thus, the data was still statistically significant in the 0.05 level.

Figure 11:
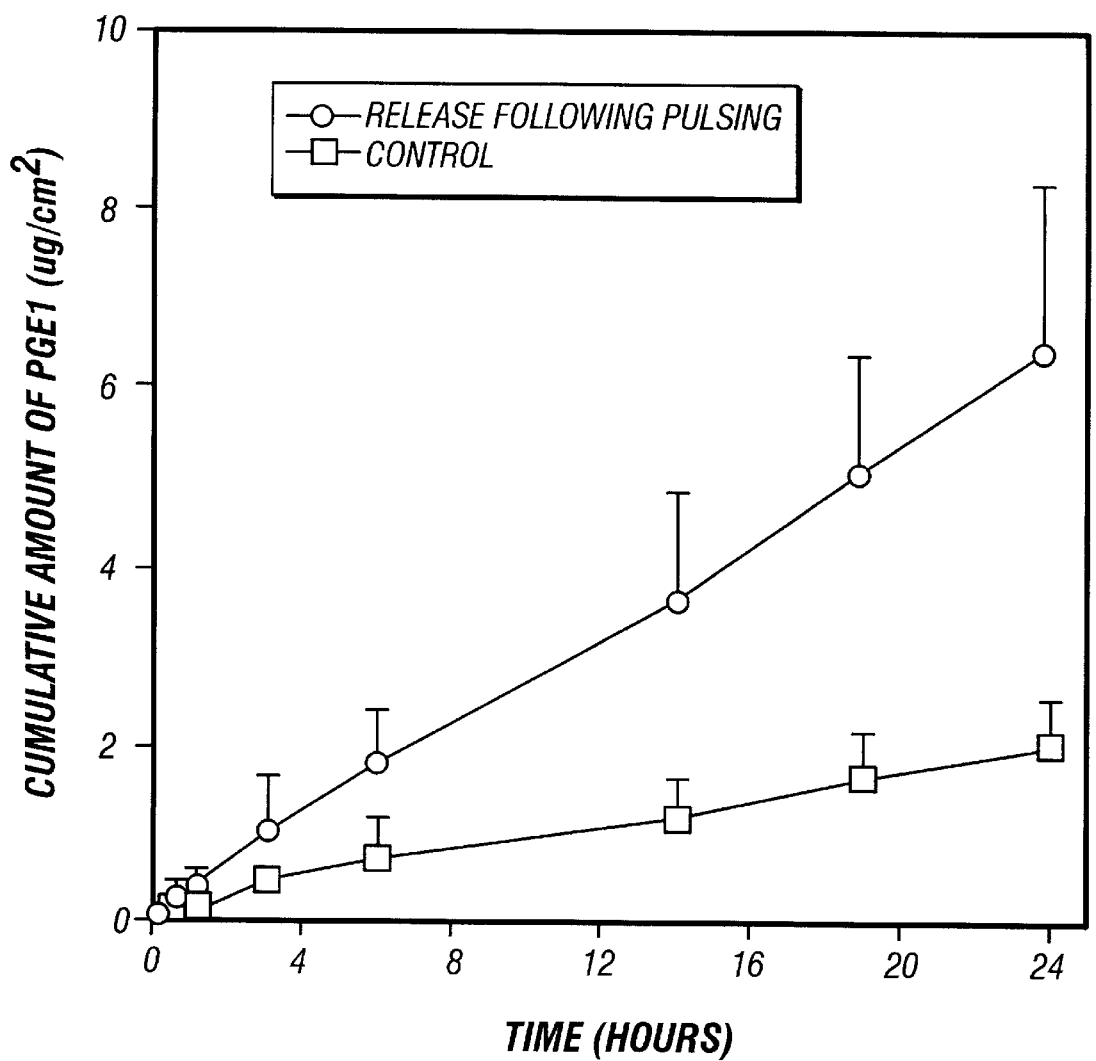
FIG. 11 shows release of PGE1 from skin following pulsing of a PGE1 suspension (300 µg/6 µl) into dermatomed skin. Error bars are as before.

When this protocol was used on dermatomed skin and sampling time was increased to 24 hours, PGE1 was found to permeate into the receiver indicating traversal of the skin. The cumulative amount of PGE1 permeated into receiver as a function of time following pulsing is shown in FIG. 11. The total amount permeated into the receiver in 24 hours was $6.43\pm2.17$ $\mu g$ for the pulsing group and $2.0\pm0.57$ $\mu g$ for the unpulsed control group. The amount of PGE1 in pulsed skin at 24 hours was $14.44\pm4.29$ $\mu g$, while in control skin was $5.68\pm3.25$ $\mu g$. The p-value on a two-tail test is 0.048. Thus, the data is statistically significant at the 0.1 level. If this data is adjusted for the amount permeated into receiver over 24 hours, then the amount of PGE1 delivered into skin following pulsing is 20.87 $\mu g$ for pulsed group and 7.68 $\mu g$ for control group. The amount in pulsed skin is about 6–7 times higher than an earlier study in which sampling was done in 15 minutes using full-thickness skin. In earlier studies (15 minutes sampling), no PGE1 was detected in receiver at the end of the study, suggesting that the drug slowly diffuses out of the skin over a period of several hours.

Another suspension study analyzed the data by immunoassay. A concentration of 100 $\mu g/8$ $\mu l$ of prostaglandin in distilled water was prepared, and the resulting product was observed to be a suspension. A volume of 8 $\mu l$ of this suspension was placed on skin for pulsing. The skin was placed on a metal plate and pulse was applied using meander electrodes under a lead weight (435 g). Pulsing studies were conducted on full-thickness human cadaver skin, using six pulses (120 V, 20 ms each). Control studies were then done in which the drug suspension was placed on skin and pressure applied for 2 minutes (to simulate the time it takes to give six pulses) but no pulse was applied. These six pieces of skin and one piece of untreated skin were then analyzed by enzyme immunoassay. The skin was not digested by the tissue solubilizer as the strong base used in these solubilizers may have deleterious effect on the stability of prostaglandins. This was not a consideration in earlier experiments as only the radioactivity (cpm) had to be quantitated following the experiment; the total cpm would not be affected even if prostaglandin degrades after the pulsing has been performed. The results show that the pulsed skin ($2.19\pm1.38$ $\mu g/cm^2$) had a higher amount of PGE1 than the unpulsed control skin ($1.19\pm0.31$ $\mu g/cm^2$). The efficiency of delivery has higher than that achieved by earlier studies with PGE1 solution or PGE1 dextran/latex particles.

Release of Drug from Pulsed Skin

Figure 12:
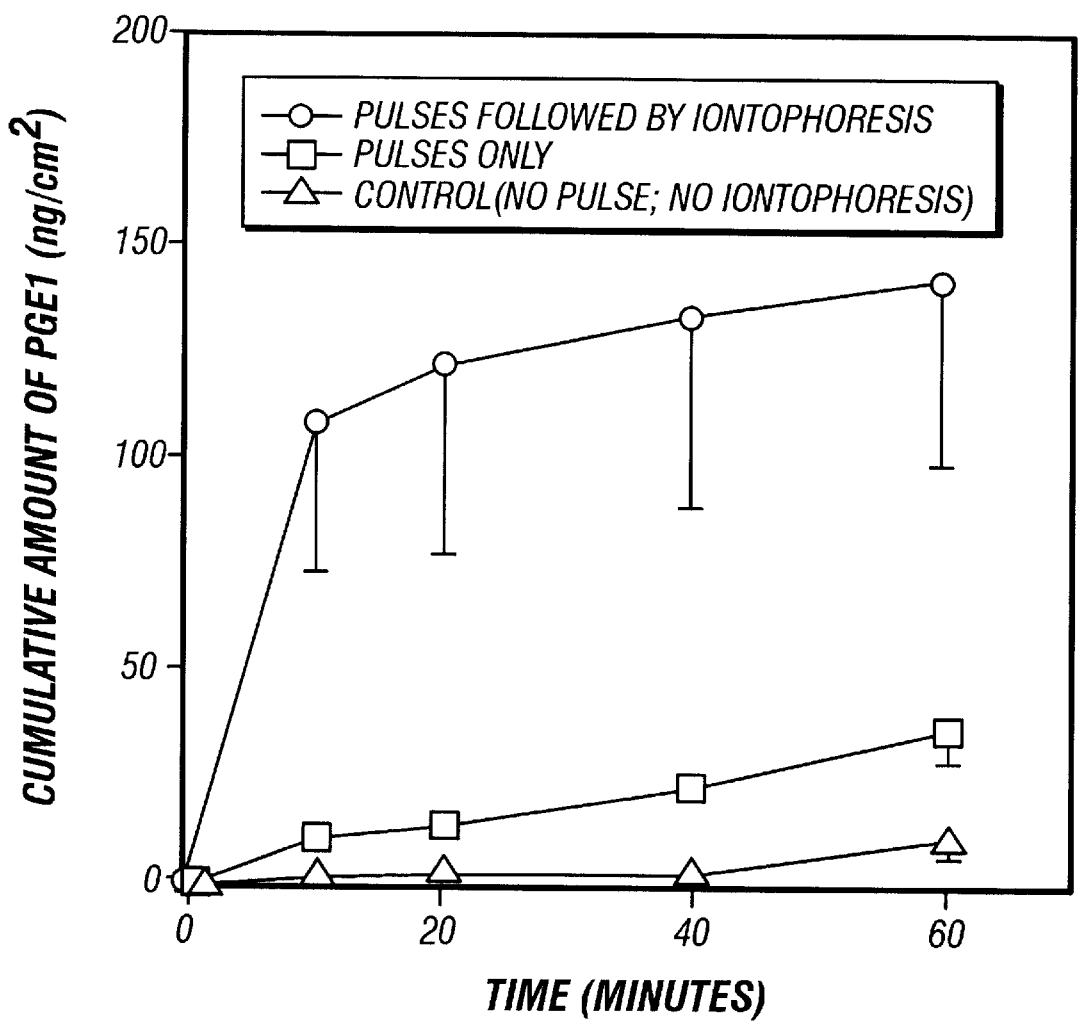
FIG. 12 shows release of PGE1 from pulsed full thickness skin with or without iontophoresis. Error bars are as before.

A concentration of 20 $\mu g/16$ $\mu l$ of prostaglandin in 7:3 ethanol:water was spiked with $^3$H-PGE, and dextran particles (5% w/v) were added to this solution. A volume of 16 $\mu l$ of this solution was placed on full-thickness human cadaver skin (six pulses, 120 V, 20 ms) were applied by meander electrodes. Following pulsing, the skin was mounted on diffusion cells and samples were taken at periodic intervals (FIG. 12). The drug was allowed to be released from pulsed skin either by itself (pulses only) or by use of iontophoresis (20 minutes) to drive out the drug reservoir (pulses followed by iontophoresis). A control study also was done in which all variables were the same but no pulse or iontophoresis was applied. As shown in FIG. 12, the unpulsed control had much lower amounts as compared to pulsed skin, with the most drug being released by iontophoresis of pulsed skin. This is most likely because iontophoresis provided the driving force to push the drug reservoir out from the skin.

Studies with Penile Skin

A therapeutic dose could also be delivered within a short period of time. To accomplish this, however, the concentration of PGE1 had to be increased. To establish that aforementioned studies are predictive of the end use of this technology (e.g., treating erectile dysfunction or inducing, enhancing or maintaining erectile function), penile skin was examined. A concentration of 1.0 mg PGE1 suspension in 6.0 $\mu l$ was used in this case. Full thickness (average thickness 0.38 mm) human cadaver penile skin was used and pulsed on the Franz cell setup as before. Six pulses (10 ms each) of 100 V each were applied. The amount of PGE1 in pulsed skin and in control skin was $19.88\pm0.93$ $\mu g$ and $15.76\pm0.05$ $\mu g$, respectively. The p-value on a two-tail test is 0.017. Thus, the data is statistically significant at the 0.05 level. The high unpulsed control value may be due to the inability to wash the skin surface properly prior to analysis or driving particles into the skin by pressure in the absence of an electric pulse.

This study was repeated using enzyme immunoassay and PGE1 directly from the vial. A concentration of 1 mg/6 $\mu l$ of prostaglandin in 10 mM phosphate buffer was prepared directly using the PGE1 material from Sigma, without any ethanol crystallization. The skin was then homogenized and extracted as before. The amount of PGE1 in pulsed skin and in control skin was $12.02\pm6.42$ $\mu g$ and $15.09\pm9.86$ $\mu g$, respectively. The p-value on a two-tail test is 0.67. Thus, the difference between pulsed and unpulsed control skin is not statistically significant. Since earlier studies gave a statistically significant difference, it appears that recrystallization from ethanol, which produces a more homogeneous drug distribution for the donor suspension, increases transdermal delivery. PGE1 directly from the vial may have a nonuniform particle size distribution, in which case the dose for each replicate will vary even though the same volume is used. Alternatively, the variation could result from skin homogenization not being very effective in releasing all the drug from the microstructure of the skin into solution. In earlier studies with PGE/³H-PGE, the skin is dissolved which will result in complete release of the drug into solution. In any case, enzyme immunoassay data is still in the therapeutic range, which indicates that the end point therapeutic use is feasible. As the data is in therapeutic range with this assay, this suggests that significant degradation to the point of losing most of the drug is not occurring. When pulsed with six 100 V (20 ms) pulses are applied with a meander electrode, the penile skin was observed to develop slight burn marks, suggesting that penile skin is more sensitive and has lower resistance than skin from other sites; thus, pulse length has to be low when using meander electrodes that are in direct contact with penile skin.

The variability between pulsed and unpulsed skin may have resulted from even one particle embedding in the skin in unpulsed control, which would significantly increase the amount of PGE1 calculated in the skin. A further confounding effect could have been due to the use of ethanol, which is a known penetration enhancer for transdermal delivery. However, it is not clear if ethanol could have exerted its effect in the short time it was on the skin before skin was digested by tissue solubilizer. Alternatively, inadequate skin washing could have increased the amount of PGE1 in unpulsed control skin.

To summarize, these studies show that PGE1 in solution can be delivered into human skin by electric pulses. Further enhancement is achieved when inert particles are mixed with the formulation and delivered with a meander electrode (i.e. electropulsing in combination with iontophoresis). If a drug suspension is used, then relatively large amounts can be delivered into human skin by high voltage pulses. Trasndermal drug delivery via electrical pulsing is potentially useful in patients who do not respond to other treatments for erectile dysfunction such as VIAGRA™, or cannot tolerate the side effects.

EXAMPLE V

This example shows that electropulsing under conditions sufficient to transdermally introduce compositions into the rabbit penis is well tolerated by human subjects.

Genetronics, Inc. has sponsored a Phase I feasibility study of human sensation tolerance on the method and the electrical apparatus (no drug was involved in this study). The institutional IRB approval and Patient Consent Form were generated prior to the study. The pain level of electrical therapy was assessed in 20 patients that had previously undergone either cavernosal injection therapy or transurethra insertion therapy, 10 patients per group. Sterile PBS was used as a placebo for all pulsing sensation tests. The setup of pulse applicator (shown in FIG. 3, where the cuff provided controlled pressure) ensured good contact between the electrodes and the skin (midshaft and partial glans).

Patients were subjected to a single pulse of 50 to 80 volts in 10 volt increments delivered for 3 msec. The patients were asked to rate the pulse sensation on a scale of 0, no pain, to 10, excruciating. The results of this study shown in FIG. 13 and are summarized as follows: (1) All patients passed single pulsation tests (50 V–80 V, 3 ms) without rating the sensation excruciating pain. (2) The pulse sensation was tolerable; from 60 V to 80 V, 77.5% of subjects rated the electropulse from no pain to discomforting and only 10% rated the sensation from distressing to horrible. (3) No side effects of pulsing were observed or reported. It was concluded that the method and apparatus are safe and acceptable to patients under electrical pulse conditions sufficient to transdermally introduce a composition into the penis.

While this invention has been described as having certain embodiments, it is understood that further modifications, uses and/or adaptations of the invention are possible, and are encompassed by the invention set forth in the following claims.

What is claimed is:

1. A method for enhancing erectile function in a subject, said method comprising applying an electric pulse to the penis and substantially contemporaneously applying a vasoactive or androgenic composition thereto, said electric pulse having sufficient strength and duration for transdermally introducing an effective amount of the composition into the penis, thereby enhancing erectile function in the subject.

2. The method of claim 1, wherein the electric pulse is applied to the penile glans.

3. The method of claim 1, wherein the electric pulse is applied to the penile shaft.

4. The method of claim 1, wherein the electric pulse has a voltage from about 50 to 80 volts.

5. The method of claim 1, wherein multiple electric pulses are applied.

6. The method of claim 1, further comprising restricting venous flow from the penis.

7. The method of claim 1, further comprising iontophoresis.

8. The method of claim 1, further comprising vibration.

9. The method of claim 1, further comprising administering a vasoactive or androgenic composition to the subject orally, by injection or transurethrally.

10. The method of claim 1, wherein said composition is a vasoactive composition selected from the group consisting of prazosin, $PGE_1$, $PGE_2$, $PGE_1$, papeverine, $PGA_1$, $PGB_1$, $PGF_1$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$, $PGI_1$, $PGI_2$, carboprost tromethamine, dinoprost tromethamine, dinoprostone, lipoprost, gemeprost, metenoprost, sulprostone, tiaprost, nitroglycerin, isosorbide dinitrate, erythrityl tetranitrate, amyl nitrate, sodium nitroprusside, molsidomine, (Z)-1-{N-methyl-N-[6-(N-methyl-ammoniohexyl)amino]}diazen-1-ium-1,2-diolate (MAHMA/NO), (Z)-1-[N-(3-ammoniopropyl)-N-(n-propyl)amino]diazen-1-ium-1,2-diolate (PAPA/NO), (Z)-1-{N-[3-aminopropyl]-N-[4-(3-aminopropylammonio)butyl]-amino}diazen-1-ium-1,2-diolate (SPER/NO), sodium (Z)-1-(N,N-diethylamino)diazenium-1,2-diolate (DEA/NO), linsidomine (SIN-1), S-nitrosothiols, S-nitroso-N-acetyl-D, L-penicillamine (SNAP), S-nitroso-N-cysteine and S-nitroso-N-glutathione (SNO-GLU), smooth muscle relaxants, leukotriene inhibitors, calcium channel blockers, α1-adrenergic antagonists, α2-adrenergic agonists, phosphodiesterase inhibitors, antihypertensive agents, angiotensin-converting enzyme (ACE) inhibitors, angiotensin II receptor antagonists, phenoxybenzamine, dibenamine, doxazosin, terazosin, phentolamine, tolazoline, prazosin, trimazosin, alfuzosin, indoramin, ergotamine analogs, ergotamine analogs, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride, diazoxide, hydralazine and minoxidil, nimodepine, pinacidil, cyclandelate, dipyridamole, isoxsuprine, chlorpromazine, haloperidol, yohimbine, trazodone, apomorphine, bromocriptine, naltrexone and vasoactive intestinal peptide.

11. The method of claim 1, wherein said composition is an androgenic composition selected from the group consisting of: androsterone, testosterone, dihydrotestosterone, dehydroepiandrosterone (DHEA), DHEA sulfate, enanthate, propionate, cypionate esters of testosterone, phenylacetate esters of testosterone, testosterone alkyls, methyltestosterone, testolactone, oxymetholone and fluoxymesterone.

12. A method for treating impotence in a subject comprising applying an electric pulse to the penis of the subject and substantially contemporaneously applying a vasoactive or androgenic composition thereto, said electric pulse having sufficient strength and duration for transdermally introducing an effective amount of the composition into the penis thereby enhancing erectile function in the subject.

13. The method of claim 12, wherein the electric pulse is applied to the penile glans.

14. The method of claim 12, wherein the electric pulse is applied to the penile shaft.

15. The method of claim 12, wherein the electric pulse has a voltage from about 50 to 80 volts.

16. The method of claim 12, wherein multiple electric pulses are applied.

17. The method of claim 12, further comprising restricting venous flow from the penis.

18. The method of claim 12, further comprising iontophoresis.

19. The method of claim 12, further comprising vibration.

20. The method of claim 12, further comprising administering a vasoactive or androgenic composition to the subject orally, by injection or transurethrally.

21. The method of claim 12, wherein said composition is a vasoactive composition selected from the group consisting of prazosin, $PGE_1$, $PGE_2$, $PGE_1$, papeverine, $PGA_1$, $PGB_1$, $PGF_1$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3$, $PGI_1$, $PGI_2$, carboprost tromethamine, dinoprost tromethamine, dinoprostone, lipoprost, gemeprost, metenoprost, sulprostone, tiaprost, nitroglycerin, isosorbide dinitrate, erythirityl tetranitrate, amyl nitrate, sodium nitroprusside, molsidomine, (Z)-1-{N-methyl-N-[6-(N-methyl-ammoniohexyl)amino]}diazen-1-ium-1,2-diolate (MAHMA/NO), (Z)-1-[N-(3-ammoniopropyl)-N-(n-propyl)amino]diazen-1-ium-1,2-diolate (PAPA/NO), (Z)-1-{N-[3-aminopropyl]-N-[4-(3-aminopropylammonio)butyl]amino}-diazen-1-ium-1,2-diolate (SPER/NO), sodium (Z)-1-(N,N-diethylamino)diazenium-1,2-diolate (DEA/NO), linsidomine (SIN-1), S-nitrosothiols, S-nitroso-N-acetyl-D, L-penicillamine (SNAP), S-nitroso-N-cysteine and S-nitroso-N-glutathione (SNO-GLU), smooth muscle relaxants, leukotriene inhibitors, calcium channel blockers, $\alpha$1-adrenergic antagonists, $\alpha$2-adrenergic agonists, phosphodiesterase inhibitors, antihypertensive agents, angiotensin-converting enzyme (ACE) inhibitors, angiotensin II receptor antagonists, phenoxybenzamine, dibenamine, doxazosin, terazosin, phentolamine, tolazoline, prazosin, trimazosin, alfuzosin, indoramin, ergotamine analogs, ergotamine analogs, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride, diazoxide, hydralazine and minoxidil, nimodepine, pinacidil, cyclandelate, dipyridamole, isoxsuprine, chlorpromazine, haloperidol, yohimbine, trazodone, apomorphine, bromocriptine, naltrexone and vasoactive intestinal peptide.

22. The method of claim 12, wherein said composition is an androgenic composition selected from the group consisting of: androsterone, testosterone, dihydrotestosterone, dehydroepiandrosterone (DHEA), DHEA sulfate, enanthate, propionate, cypionate esters of testosterone, phenylacetate esters of testosterone, testosterone alkyls, methyltestosterone, testolactone, oxymetholone and fluoxymesterone.

23. A method for delivering a composition into the penis of a subject comprising applying an electric pulse to the penis and substantially contemporaneously applying the composition to the penis, said electric pulse having sufficient strength and duration for transdermally introducing the composition into the penis in an amount greater than provided by passive diffusion of the composition into the penis when applied thereto.

* * * * *